US008546578B2

(12) United States Patent (10) Patent No.: US 8,546,578 B2
DiMagno (45) Date of Patent: Oct. 1, 2013

(54) IODONIUM CYCLOPHANES FOR SECURE ARENE FUNCTIONALIZATION

(75) Inventor: Stephen DiMagno, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 61 days.

(21) Appl. No.: 13/021,182

(22) Filed: Feb. 4, 2011

(65) Prior Publication Data

US 2011/0190505 A1 Aug. 4, 2011

Related U.S. Application Data

(60) Provisional application No. 61/301,491, filed on Feb. 4, 2010.

(51) Int. Cl.
*C07D 211/80* (2006.01)
(52) U.S. Cl.
USPC .......................................................... 546/285
(58) Field of Classification Search
None
See application file for complete search history.

(56) References Cited

U.S. PATENT DOCUMENTS

| | | | |
|---|---|---|---|
| 8,377,704 | B2 | 2/2013 | DiMagno et al. |
| 2005/0226776 | A1 | 10/2005 | Brady et al. |
| 2006/0120958 | A1 | 6/2006 | Brady et al. |
| 2006/0128031 | A1 | 6/2006 | Robotti et al. |
| 2006/0292060 | A1 | 12/2006 | Wadsworth et al. |
| 2007/0092441 | A1 | 4/2007 | Wadsworth et al. |
| 2009/0286992 | A1 | 11/2009 | Carroll et al. |
| 2011/0091982 | A1 | 4/2011 | DiMagno et al. |
| 2011/0144344 | A1 | 6/2011 | Woodcraft |
| 2011/0190505 | A1 | 8/2011 | DiMagno |
| 2011/0313170 | A1 | 12/2011 | DiMagno |
| 2012/0004417 | A1 | 1/2012 | DiMagno |

FOREIGN PATENT DOCUMENTS

| | | |
|---|---|---|
| WO | WO 2003/002157 | 1/2003 |
| WO | WO 2005/021472 | 3/2005 |
| WO | WO 2005/061415 | 7/2005 |
| WO | WO 2005/097713 | 10/2005 |
| WO | WO 2008/082695 | 7/2008 |
| WO | WO 2010/008522 | 1/2010 |
| WO | WO 2010/048170 | 4/2010 |

OTHER PUBLICATIONS

U.S. Appl. No. 12/907,079, filed Oct. 19, 2010, DiMagno et al.
U.S. Appl. No. 13/125,209, filed Jul. 6, 2011, DiMagno.
U.S. Appl. No. 13/172,953, filed Jun. 30, 2011, DiMagno.
Authorized Officer H. Sahagun Krause. Extended European Search Report in International Application No. PCT/US2009/061308, dated Feb. 23, 2012, pages.
Authorized Officer Young Jin Kang, PCT/US2009/061308, International Search Report and Written Opinion of the International Searching Authority, mailed Apr. 30, 2010, 9 pages.
Authorized Officer Gijsbertis Beijer, PCT/US2009/061308, International Preliminary Report on Patentability, issued Apr. 26, 2011, 7 pages.
Abboud et al., "Hydrogen Bonding in the Gas Phase and in Solution. New Experimental Developments," *Quantitative Treatments of Solute/Solvent Interactions,* Polarizer and Murray Ed. Elsevier: Amsterdam, 1994, pp. 134-179.
Adams et al., "Nucleophilic routes to selectively fluorinated aromatics," *Chem. Soc. Rev.,* 1999, 28:225-231.
Albrecht et al., "Structural Versatility of Anion—π Interactions in Halide Salts with Pentafluorophenyl Substituted Cations," *J. Am. Chem. Soc.,* 2008, 130:4600-01.
Al-Qahtani et al., "Palladium(II)-mediated 11C-carbonylative coupling of diaryliodonium salts with organostannanes. A new, mild and rapid synthesis of aryl [11C]ketones.," *J. of Chem Soc. Perkin Transactions 1,* 2000, 1033-1036.
Bailly et al., "Pentafluorophenyliodine(III) compounds. Part 3. (Pentafluorophenyl)iodine difluoride: alternative preparations, molecular structure, and properties," *Z Anorg. Allg. Chem.,* 2000, 626:1406-1413.
Bielawski et al., "High-yielding one-pot synthesis of diaryliodonium triflates from arenes and iodine or aryl iodides," *Chem. Commun.,* 2007, 2521-2523.
Biffinger et al., "The Polar Hydrophobicity of Fluorinated Compounds," *ChemBioChem,* 2004, 5:622-627.
Bini et al., "Development of Cation/Anion 'Interaction' Scales for Ionic Liquids through ESI-MS Measurements," *J. Phys. Chem. B,* 2007, 111(3):598-604.
Blondel et al., "Electron spectrometry at the μeV level and the electron affinities of Si and F," *J. Phys. B: At., Mol. Opt. Phys.,* 2001, 34:2757.
Boechat et al., "Fluorodenitrations using tetramethylammonium fluoride," *J. Chem. Soc., Chem. Commun.,* 1993, 921-922.
Cai et al., "Chemistry with [18F]fluoride ion," *European Journal of Organic Chemistry,* 2008, 17:2853-2873.
Cerioni et al., "Solution structure of bis(acetoxy)iodoarenes as observed by $^{17}$O NMR spectroscopy," *Tetrahedron Lett.,* 2004, 45:505-507.
Choudhury et al., "Crystal engineering via C-H F and C-H π interactions in two substituted indoles," *Acta Cryst.,* 2004, C60:o644.
Christe et al., "Quantitative Measure for the 'Nakedness' of Fluoride Ion Sources," *J. Am. Chem. Soc.,* 2003, 125:9457-9461.
Christe et al., "Syntheses, properties, and structures of anhydrous tetramethylammonium fluoride and its 1:1 adduct and trans-3-amino-2-butenenitrile," *J. Am. Chem. Soc.,* 1990, 112:7619-25.
Ciufolini et al., "Oxidative amidation of phenols through the use of hypervalent iodine reagents," *Development and applications. Synthesis,* 2007, 3759-3772.
Crivello, "A new visible light sensitive photoinitiator system for the cationic polymerization of epoxides," *J. Polym. Sci., Part A: Polym. Chem.,* 2009, 47:866-875.

(Continued)

*Primary Examiner* — Janet Andres
*Assistant Examiner* — Heidi Reese
(74) *Attorney, Agent, or Firm* — Fish & Richardson P.C.

(57) ABSTRACT

This disclosure relates to compounds, reagents, and methods useful in the synthesis of aryl fluorides, for example, in the preparation of $^{18}$F labeled radiotracers. For example, this disclosure provides universal "locked" aryl substituents that result in StereoElectronic Control of Unidirectional Reductive Elimination (SECURE) from diaryliodonium salts. The reagents and methods provided herein may be used to access a broad range of compounds, including aromatic compounds, heteroaromatic compounds, amino acids, nucleotides, and synthetic compounds.

83 Claims, 1 Drawing Sheet

(56) References Cited

OTHER PUBLICATIONS

Crivello, "Photoactivated cationic ring-opening frontal polymerization of oxetanes," *Polym. Prepr. (Am. Chem. Soc., Div. Polym. Chem.)* 2006, 47:208-209

Curran, D. P. et al. "Experimental techniques in fluorous synthesis: A user's guide," *Comb. Chem.*, 2000, 327-352.

Darses et al., "Potassium organotrifluoroborates. New partners in palladium-catalyzed cross-coupling reactions.," *Eur. J. Org. Chem.*, 1999, 1875-1883.

Darses et al., "Potassium trifluoro(organo)borates: New perspectives in organic chemistry," *Eur. J. Org. Chem.*, 2003, 4313-4327

Davies et al., "Ab initio and DFT computer studies of complexes of quaternary nitrogen cations: trimethylammonium, tetramethylammonium, trimethylethylammonium, choline and acetylcholine with hydroxide, fluoride and chloride anions," *Phys. Chem. Chem. Phys.*, 2003, 5:4533-4540.

DiMagno et al., "Facile Synthesis of meso-Tetrakis(perfluoroalkyl)porphyrins: Spectroscopic Properties and X-ray Crystal Structure of Highly Electron-Deficient 5,10,15,20—Tetrakis(heptafluoroproyl)porphyrin," *J. Org. Chem.*, 1994, 59:6943.

DiMagno et al., "The Strength of Weak Interactions: Aromatic Fluorine in Drug Design," *Curr. Top. Med. Chem.*, 2006, 6:1473-1482.

Dohi et al., "A chiral hypervalent iodine(III) reagent for enantioselective dearomatization of phenols," *Angew. Chem. Int. Ed. Engl*, 2008, 47,:3787-90.

Ermert et al, "Comparison of pathways to the versatile synthon of no-carrier-added 1-bromo-4-[18F]fluorobenzene," *Journal of Labelled Compounds & Radiopharmaceuticals* 2004, 47, 429-441.

Fernandez et al., "Multinuclear PG SE Diffusion and Overhauser NMR Studies on a Variety of Salts in THF Solution," *Inorg. Chem.*, 2005, 44:5509-5513.

Frohn et al., "Preparation of polyfluorinated cycloalk-1-enyl-, alk-l-enyl-, and alkyliodine tetrafluorides using XeF2 in the presence of appropriate Lewis acids as fluorooxidant," *J. Fluorine. Chem.*, 2005, 126:1036-1043.

Giroldo et al., "An Unusually Fast Nucleophilic Aromatic Displacement Reaction: The Gas-Phase Reaction of Fluoride Ions with Nitrobenzene," *Angew Chem. Int. Ed.*, 2004, 43:3588-3590.

Gnann et al., "Naked Fluoride Ion Sources: Synthesis, Characterization, and Coupling Reaction of 1-Methylhexamethylenetetramine Fluoride," *J. Am. Chem. Soc.*, 1997, 119:112-115.

Hansch et al., "A survey of Hammett substituent constants and resonance and field parameters," Chem. Rev., 1991, 91(2):165-195.

Hof et al., "A Weak Attractive Interaction between organic Fluorine and an Amide Group," *Angew. Chem. Int. Ed.*, 2004, 43:5056-5059.

Hossain et al., "Reaction of iodoarenes with potassium peroxodisulfate/trifluoroacetic acid in the presence of aromatics. Direct preparation of diaryliodonium triflates from iodoarenes," *Tetrahedron*, 2006, 62:6955-6960.

Huang et al., "Synthesis of ether-linked fluorocarbon surfactants and their aggregational properties in organic solvents," *Journal of Colloid and Interface Science*, 2004, 272:457-464.

Kang et al., "Palladium-catalyzed coupling and carbonylative coupling of silyloxy compounds with hypervalent iodonium salts," *Tetrahedron Lett.*, 1997, 38:1947-1950.

Kang et al., "Palladium-Catalyzed Cross-Coupling of Organoboron Compounds with Iodonium Salts and Iodanes," *J. Org. Chem.*, 1996, 61:4720-4724.

Kazmierczak et al., "A simple, two-step conversion of various iodo arenes to (diacetoxyiodo) arenes with chromium(VI) oxide as the oxidant," *Synthesis*, 1998, 1721-1723.

Kazmierczak et al., "Syntheses of (diacetoxyiodo)arenes or iodylarenes from iodoarenes, with sodium periodate as the oxidant," *Molecules*, 2001, 6:881-891.

Ko et al., "Fluorous-Based Carbohydrate Microarrays," *J. Am. Chem. Soc.* 2005, 127, 13162-13163.

Kornath et al., "Tetramethylphosphonium Fluoride: 'Naked' Fluoride and Phosphorane," *Inorg. Chem.*, 2003, 42:2894-2901.

Kraszkiewicz et al., "Facile syntheses of symmetrical diaryliodonium salts from various arenes, with sodium metaperiodate as the coupling reagent in acidic media," *Synthesis*, 2008, 2373-2380.

Lubinkowski et al., "Reactions of diaryliodonium fluoroborates with inorganic anions," *J. Org. Chem.*, 1978, 43:2432-2435

Lummis et al., "A Cation-π Binding Interaction with a Tyrosine in the Binding Site of the $GABA_c$ Receptor," *Chemistry & Biology*, 2005, 12:993-997.

McMillen et al., "Hydrocarbon Bond Dissociation Energies," *Ann. Rev. Phys. Chem.*, 1982, 33:493 (abstract only).

McKillop et al., "Further functional-group oxidations using sodium perborate," *Tetrahedron*, 1989, 45:3299-306.

Merritt et al., "Diaryliodonium Salts: A Journey from Obscurity to Fame," *Angew. Chem., Int. Ed.*, 2009, 48:9052-9070.

Moore et al., "Hypervalent iodine-promoted phenolic oxidations: Generation of a highly versatile o-quinone template," *Chemtracts*, 2002, 15:74-80.

Moriarty et al., "Oxidation of phenolic compounds with organohypervalent iodine reagents," *Org. React.*, 2001, 57:327-415.

Okuyama et al., "Solvolysis of Cyclohexenyliodonium Salt, a New Precursor for the Vinyl Cation: Remarkable Nucleofugality of the Phenyliodonio Group and Evidence for Internal Return from an Intimate Ion-Molecule Pair," *J. Am. Chem. Soc.*, 1995, 117:3360-7.

Olsen et al., "A Fluorine Scan of Thrombin Inhibitors to Map the Fluorophilicity/Fluorophobicity of an Enzyme Active Site: Evidence for CF•••C¼O Interactions," *Angew Chem.*, 2003, 115:2611.

Padelidakis et al., "Synthesis and characterization of 2,6-difluorophenyliodide(III) derivatives," *J. Fluorine Chem.*, 1999, 99:9-15.

Page et al., "Simple direct synthesis of [bis(trifluoroacetoxy)iodo]arenes," *Synthesis*,2006, 3153-3155.

Pearson et al., "Nucleophilic reactivity constants toward methyl iodide and trans-dichlorodi (pyridine)platinum(II)," *J. Am. Chem. Soc.*, 1968, 90:319-326.

Pike et al, "Reactions of cyclotron-produced [$^{18}$F]fluoride with diaryliodonium salts—a novel single-step route to no-carrier-added [$^{18}$F]fluoroarenes," *Journal of the Chemical Society, Chemical Communications*, 1995, 2215-2216.

Plenio et al., "The Coordination Chemistry of Fluorocarbons: Difluoro-m-cyclophance-Based Fluorocryptands and Their Group I and II Metal Ion Complexes," *Inorg. Chem.*, 1997, 36:5722.

Quideau et al., "Chemical and electrochemical oxidative activation of arenol derivatives for carbon-carbon bond formation," *Curr. Org. Chem.*, 2004, 8:113-148.

Ross et al, "Nucleophilic 18F-Fluorination of Heteroaromatic Iodonium Salts with No-Carrier-Added [18F]Fluoride," *Journal of the American Chemical Society*, 2007, 129, 8018-8025.

Ryan et al., "Direct α-arylation of ketones: the reaction f cyclic ketone enolates with diphenyliodonium triflate," *Tetrahedron Lett.*, 1997, 38:5061-5064.

Sánchez et al., "Regioselective functionalisation of nitrobenzene and benzonitrile derivatives via nucleophilic aromatic substitution of hydrogen by phosphorus-stabilized carbanions," *Tetrahedron*, 2006, 62:3648-3662.

Schwesinger et al., "Stable Phosphazenium Ions in Synthesis—an Easily Accessible, Extremely Reactive 'Naked' Fluoride Salt," *Angew. Chem., Int. Ed. Engl.*, 1991, 30:1372.

Seppelt, "Does the Naked Fluoride Ion Exist?" *Angew. Chem., Int. Ed. Engl.*, 1992, 31:292.

Shah et al, "The synthesis of [18F]fluoroarenes from the reaction of cyclotron-produced [18F]fluoride ion with diaryliodonium salts," *Journal of the Chemical Society, Perkins Transactions I* 1998, 2043-2046.

Sharefkin et al., "Iodosobenzene Diacetate," *Org. Synth,.* 1963, 43, No pp. given.

Stoyanov et al., "An Infrared vNH Scale for Weakly Basic Anions. Implications for Single-Molecule Acidity and Superacidity," *J. Am. Chem. Soc.*, 2006, 128:8500-8508.

Sun et al., "A Method for Detecting Water in Organic Solvents," *Org. Lett.*, 2008, 10:4413-4416.

Sun et al., "Anhydrous Tetrabutylammonium Fluoride," *J. Am. Chem. Soc.*, 2005, 127:2050-2051.

Sun et al., "Competitive demethylation and substitution in N,N,N-trimethylanilinium fluorides," *J. Fluor. Chem.*, 2007, 128:806-812.

Sun et al., "Fluoride relay: a new concept for the rapid preparation of anhydrous nucleophilic fluoride salts from KF," *Chem. Commun.*, 2007, 528-529.

Sun et al., "Room-Temperature Nucleophilic Aromatic Fluorination: Experimental and Theoretical Studies," *Angew. Chem. Int. Ed.*, 2006, 45:2720-2725.

Sun et al., "Rapid Preparation of Fluorinated Aromatic Heterocycles," *ACS symposium series*, 2009, 1003:85-104.

Thalladi et al., "C-H•••F Interactions in the Crystal Structures of Some Fluorobenzenes," *J. Am. Chem. Soc.*, 1998, 120:8702-8710.

Thayer, "Fabulous Fluorine: Having fluorine in life sciences molecules brings desirable benefits, but the trick is getting it in place and making south—after building blocks," *C&E News*, 2006, 84:15-24.

Toba, "The design of photoinitiator systems," *J. Photopolym. Sci. Technol.*, 2003, 16:115-118.

Tohma et al., "Preparation and reactivity of 1,3,5,7-tetrakis[4-(diacetoxyiodo)phenyl]adamantane, a recyclable hypervalent iodine(III) reagent," *Angew. Chem., Int. Ed.*, 2004, 43:3595-3598.

Tsuzuki et al., "Magnitude and orientation dependence of intermolecular interaction between perfluoroalkanes: High level ab initio calculations of $CF_4$ and $C_2F_6$ dimers," *J. Chem. Phys., 2002*, 116:3309-3315.

Tsuzuki et al., "Magnitude and orientation dependence of intermolecular interaction of perfluoropropane dimer studied by high-level ab initio calculations: comparison with propane dimer," *J. Chem. Phys.*, 2004, 121:9917-9924.

Tsuzuki et al., "Magnitude of Interaction between n-Alkane Chains and Its Anisotropy: High-Level ab Initio Calculations of n-Butane, n-Petane, and n- Hexane Dimers," *J. Phys. Chem. A*, 2004,108:10311-10316.

Uyanik et al., "Enantioselective Kita Oxidative Spirolactonization Catalyzed by In Situ Generated Chiral Hypervalent Iodine(III) Species," *Angew. Chem., Int. Ed.*, 2010, 49, 2175-2177, S2175/1-S2175/79.

Van Der Puy et al., "Conversion of diaryliodonium salts to aryl fluorides," *Journal of Fluorine Chemistry*, 1982, 21:385-392.

Wang et al., "Improved Arene Fluorination Methodology for I(III) Salts," *Organic Letters*, 2010, 12(15):3352-3355.

Wenthold et al., "Bond Dissociation Energies of $F2^-$ and $HF2^-$. A Gas-Phase Experimental and 62 Theoretical Study," *J. Phys. Chem.*, 1995, 99:2002-2005.

Ye et al., "Straightforward Syntheses of Hypervalent Iodine (III) Reagents Mediated by Selectfluor," *Org. Lett.*, 2005, 7:3961-3964.

Zhan et al., "Hydration of the Fluoride Anion: Structures and Absolute Hydration Free Energy from the First-Principles Electronic Structure Calculations," *J. Phys. Chem. A*, 2004, 108, 2020-2029.

Zhang et al., "A practical route for synthesizing a PET ligand containing [$^{18}$F] fluorobenzene using reaction of diphenyliodonium salt with [$^{18}$F]F$^-$," *Tetrahedron Letters*, 2007, 48(49):8632-8635.

Zhang et al., "Diels-Alder reaction and double phenylation in reaction of thiophenes with diphenyliodonium triflate," *Heterocycles*, 2004, 64:199-206.

Zhdankin et al., "Chemistry of Polyvalent Iodine," *Chem. Rev.*, 2008, 108:5299-5358.

Zhong et al., "From ab initio quantum mechanics to molecular neurobiology: A cation-π binding site in the nicotinic receptor," *PNAS*, 1998, 95:12088-12093.

Zielinska et al., "Easy preparation of (diacetoxyiodo)arenes from iodoarenes with sodium percarbonate as the oxidant," *Molecules*, 2002, 7:806-809.

Authorized Officer H. Sahagun Krause. Extended European Search Report in International Application No. 12185395.6, dated Nov. 16, 2012, 6 pages.

International Search Report and Written Opinion in International Application No. PCT/US2012/044954, mailed Feb. 13, 2013, 9 pages.

Comments Received from Third Party re Original Claims—Interpretations and Summaries, PCT/US2009/061308, Feb. 28, 2013, 488 pages.

Third Party Observation for Application No. EP20090822555, Feb. 28, 2013, 592 pages.

Observations related to Publication EP234997 and EP2537826, Feb. 28, 2013, 583 pages.

Beringer et al., "Diaryliodonium Salts. II. The Phenylation of Organic and Inorganic Bases," Phenylation Org. Inorg. Bases, Jun. 1953, 75:2708-2712.

Cai et al., "Chemistry with [18F]fluoride ion," Eur J Org Chem, 2008, 17:2853-2873.

Carroll et al., "An ab initio and MNDO-d SCF-MO computational study of stereoelectronic control in extrusion reactions of $R_2$I-F iodine(III) intermediates," J. Chem. Soc. Perkins Trans. 2, 1999, 2707-2714.

Carroll et al., "Radical scavengers: A practical solution to the reproducibility issue in the fluoridation of diaryliodonium salts," *J Fluorine Chem.*, 2007, 128:127-132.

Carroll et al., "Studies towards 6-[$^{18}$F]Fluorodopa using Iodonium Salts: Preparation of 6-Fluoro-mTyramine," *J Label Compd Radiopharm.*, 2005, 48:519-546 (abstract).

Chen and Koser, "Direct and Regiocontrolled Synthesis of alph-Phyenyl Ketones from Silyl Enol Ethers and Diphenyliodonium Fluoride," J. Org. Chem., 1991, 56:5764-5767.

Conway et al., "Iodonium Chemistry: Scope and Selectivity in Aromatic Nucleophilic Labelling Reactions," J Label Compd Radiopharm., 2005, 48:S193 (Abstract).

Ermert et al, "Comparison of pathways to the versatile synthon of no-carrier-added 1-bromo-4- [$^{18}$F]fluorobenzene," *J Labelled Compd Radiopharm*, 2004, 47:429-441.

Ermolenko et al., "Nucleophilic Substitution in Iodonium Derivatives of Indole," *Chem Heterocyclic Compounds*, Jul. 1978, 14(7):752-754.

Gail et al., "Direct N.C.A. 18F-Fluorination of Halo- and alkylarenes via corresponding diphenyloidonium salts," J. Label. Compd. Radiopharm. (Symposium Abstracts), 1997, 40:50-52.

Grushin et al., "Arylation of anions with diarylhalonium fluoroborates under conditions of interphase catalysis," *Bulletin of the Academy of Sciences of the UUSR. Division of Chemical Science, Consultants Bureau*, 1984, 33(10):2130-2135.

Grushin, "Carboranylhalonium Ions: From Striking Reactivity to a Unified Mechanistic Analysis of Polar Reactions of Diarylhalonium Compounds," *Acc. Chem. Res.*, 1992, 25:529-536.

Grushin et al., "Unified Mechanistic Analysis of Polar Reactions of Diaryliodonium Salts," J. Chem. Soc. Perkin Trans. 2, 1992, 505-511.

Hostetler et al., "Synthesis of 2[18F]Fifluoroestradiol, a Potential Diagnostic Imaging Agent for Breast Cancer: Strategies to Achieve Nucleophilic Substitution of an Electron-Rich Aromatic Ring with [18F]F-," J. Org. Chem., 1999, 64:178-185.

Iwama et al., "Regiocontrolled Synthesis of Carbocycle-Fused Indoles via Arylation of Silyl Enol Ethers with o-Nitrophenylphenyliodonium Fluoride," *Organic Left.*, 1999, 1(4):673-676.

Jang et al., "Nucleophilic Aromatic ($^{18}$F)Fluorination of Electron-Rich Aromatic System Using Iodonium Salt," *J. Label. Compd. Radiopharm.*, 2007, 50:S210 (abstract).

Lubinkowski et al., "Reactions of Diaryliodonium Salts with Sodium Alkoxides," J. Org. Chem., 1975, 40(21):3010-3015.

Martin-Santamaria et al., "Fluoridation of heteroaromatic iodonium salts—experimental evidence supporting theoretical prediction of the selectivity of the process," Chem. Commun., 2000, 649-650.

Merritt et al., "Diaryliodonium Salts: A Journey from Obscurity to Fame," *Angew. Chem., Int. Ed.*,.2009, 48:9052-9070.

Miller et al., "Synthesis of $^{11}$C, $^{18}$F, $^{15O, and}$ $^{13}$N Radiolabels for Positron Emission Tomography," *Angew. Chem. Int. Ed.*, 2008, 47:8998-9033.

Oh et al., "Highly Efficient Arylation of Malonates with Diaryliodonium Salts," J. Org. Chem., 1999, 64:1338-1340.

Pike et al, "Reactions of cyclotron-produced [18F]fluoride with diaryliodonium salts—a novel single-step route to no-carrier-added [18]fluoroarenes," J Chem Soc, ChemCommun, 1995, 2215-2216.

Ross et al, "Nucleophilic $^8$F-Fluorination of Heteroaromatic Iodonium Salts with No-Carrier-Added [$^{18}$F]Fluoride," *J Am Chem Soc*, 2007, 129:8018-8025.

Ross et al., "N.C.A. $^{18}$F-Fluorination of Various Arenes via Aryl(2-Thienyl)Iodonium Salts " *J Label Compd Radiopharm.*, 2005, 48:S153 (Abstract).

Ross, "Direct no-carrier added 18F-labelling of arenes via nucleophilic susbtitution on aryl(2)-thienyl)iodonium salts," Institute of Nuclear Medicine, Julich, Germany, Thesis, 2006, 10 pages (table of contents).

Shah et al., "Synthesis of substituted diaryliodonium salts and investigation of their reactions with no-carrier-added [$^{18}$F]Fluoride," *J. Label. Compd. Radiopharm. (Symposium Abstracts)*, 1997, 40:65-67.

Shah et al, "The synthesis of [$^{18}$F]fluoroarenes from the reaction of cyclotron-produced [$^{18}$F]fluoride ion with diaryliodonium salts," *J Chem Soc, Perkins Transactions I*, 1998, 2043-2046.

Stang and Zhdankin, "Organic Polyvalent Iodine Compounds," Chem. Rev., 1996, 96:1123-1178.

Van Der Puy et al., "Conversion of diaryliodonium salts to aryl fluorides," 21:385-392 *J Fluorine Chem*, 1982, 21:385-392.

Varvoglis et al., *Hypervalent Iodine in Organic Synthesis*, Academic Press 1997, 1 page (table of contents).

Varvoglis and Spyroudis, "Hypervalent Iodine Chemistry: 25 years of Development at the University of Thessaloniki," *Synlett*, Mar. 1998, 221-232.

Wirth, "Hypervalent Iodine Chemistry: Modern Developments in Organic Synthesis," *Topics in Current Chem.*, 2003, 7 pages (table of contents).

Wirth and Hirt, "Hypervalent Iodene Compounds: Recent Advances in Synthetic Applications," *Synthesis*, 1999, 8:1271-1287.

Wust et al., "Synthesis of novel arylpyrazolo corticosteroids as potential ligands for imaging brain glucocorticoid receptors," *Steroids*, 2003, 68:177-191.

Wust et al., "Synthesis of $^{18}$F-labelled cyclooxygenase-2 (COX-2) inhibitors via Stille reaction with 4-[$^{18}$F]fluoroiodobenzene as radiotracers for positron emission tomography (PET), " *Org. Biomol Chem.*, 2005, 3:503-507.

Wust and Kniess, "Synthesis of 4-[$^{18}$F]fluoroiodobenzene and its application in sonogashira cross-coupling reactions," *J Label Compd Radiopharm.*, 2003, 46:699-713.

Wust et al., "PET-Corticosteroids as potential ligands for mapping brain glucocorticoid receptors (GR)," *J Label Compd Radiopharm.*, 2001, 44:457-459.

Wust and Kniess, "No-carrier added synthesis of $^{18}$F-labelled nucleosides using Stille cross-coupling reactions with 4-[$^{18}$F]fluoroiodobenzene," *J Label Compd Radiopharm.*, 2004, 47:457-468.

Zhang et al., "A practical route for synthesizing a PET ligand containing [18F] fluorobenzene using reaction of diphenyliodonium salt with [18F]F-," Tetrahedron Letters, 2007, 48(49):8632-8635.

Zhang et al., "Practical Synthesis of (18F)Fluorobenzene starting from Phenyltributystanne," J. Label. Compd. Radiopharm., 2007, 50:S152.

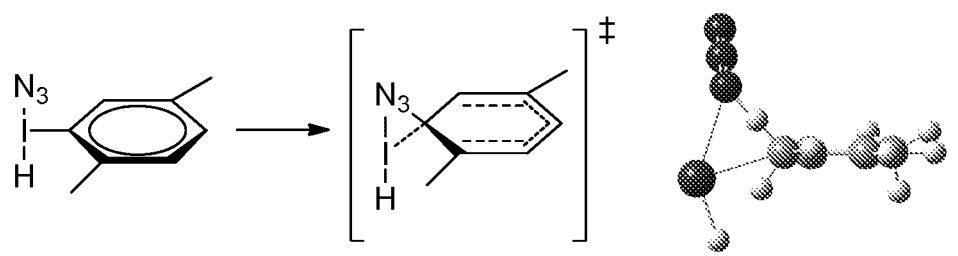
$\Delta G^{\ddagger}$ = 13.7 kcal/mol
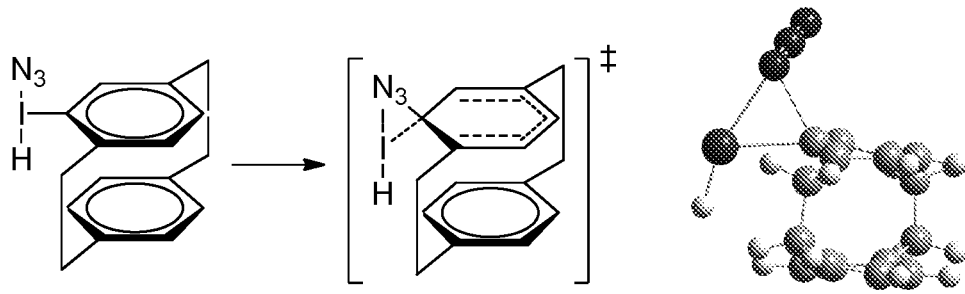
$\Delta G^{\ddagger}$ = 18.5 kcal/mol

IODONIUM CYCLOPHANES FOR SECURE ARENE FUNCTIONALIZATION

CROSS-REFERENCE TO RELATED APPLICATIONS

This application claims priority under 35 U.S.C. §119(e) to U.S. Provisional Application Ser. No. 61/301,491, filed on Feb. 4, 2010, which is incorporated by reference in its entirety herein.

TECHNICAL FIELD

This disclosure relates to compounds, reagents, and methods useful in the synthesis of aryl fluorides, for example, in the preparation of $^{18}$F labeled radiotracers. The reagents and methods provided herein may be used to access a broad range of compounds, including aromatic compounds, heteroaromatic compounds, amino acids, nucleotides, and synthetic compounds.

BACKGROUND

Aryl fluorides are structural moieties in natural products as well as a number of therapeutically important compounds, including positron emission tomography (PET) tracers and pharmaceuticals. Therefore methods and reagents for producing such aryl fluorides, for example efficient methods for producing aryl fluorides, are desirable.

SUMMARY

Provided herein are methods of preparing substituted aryl and heteroaryl ring systems using iodonium cyclophane compounds, salts, and intermediates. For example, iodonium cyclophane salts and iodonium cyclophane fluorides, as provided herein, can undergo decomposition to prepare an aryl fluoride. In the thermal decomposition of unsymmetrial diaryliodonium salts, the identity of the aryl iodide reductively eliminated it typically dictated by electronic effects; for example, the electron-rich aryl iodide and the functionalized electron-poor aromatic compound are formed predominantly (see, for example, WO 2010/048170, which is incorporated by reference herein). This disclosure provides universal "locked" aryl substituents that result in StereoElectronic Control of Unidirectional Reductive Elimination (SECURE) from diaryliodonium salts. Since electronic effects cannot be used exclusively to achieve this end, steric and/or stereoelectronic effects can be exploited to gain regiocontrol of reductive elimination.

Provided herein are aryl ligands on iodine that can generate a highly strained reductive elimination transition state. This strained transition state is created through the introduction of significant steric congestion above and/or below the aromatic ring in conjunction with little steric congestion in the plane of the ring. For example, [2.2]paracyclophane iodine(III) salts are described herein.

In some embodiments, the iodonium cyclophane compound can be a compound of Formula (1):

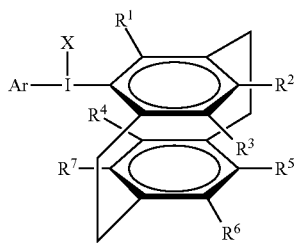

or Formula (4):

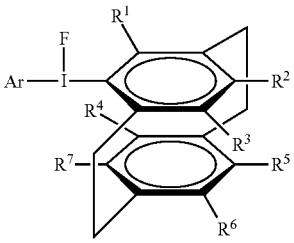

wherein:

Ar is a substituted or unsubstituted aryl or heteroaryl ring system;

X is either a moiety wherein the pKa of the acid H—X is less than 12 or a leaving group;

$R^1$ is hydrogen or a substituent having a Hammett $\sigma_p$ value of less than zero; and $R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, $-SR^8$, $-SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_n NR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, and $(L)_p$-Z, or one or more of $R^2$ and $R^3$, $R^4$ and $R^7$, and $R^5$ and $R^6$ come together to form a fused cycloalkyl, heterocycloalkyl, aryl, or heteroaryl ring system;

each m, n, and p are independently an integer from 0 to 10;

each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

L is a linker; and

Z is a solid support.

The X moiety can be one wherein the pKa of the acid H—X is less than 12. In some embodiments, X is selected from the group consisting of halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, X can be selected from the group consisting of: fluoride, chloride, bromide, iodide, triflate, trifluoroacetate, benzoate, acetate, phenoxide, trifluoroethoxide, cyanate, azide, thiocyanate, thiolates, phosphates, and stabilized enolates. In some embodiments, X can comprise a radioactive isotope. For example, X can be F or a radioactive isotope of F (i.e., $^{18}$F).

In some cases, X is a leaving group. For example, X can be selected from the group consisting of: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, chloride, bromide, and iodide.

The aryl rings on the cyclophane moiety can be substituted or unsubstituted. In some embodiments, $R^1$ is selected from the group consisting of: $-(C_1-C_{10})$alkyl, $-(C_1-C_{10})$haloalkyl, $(C_2-C_{10})$alkenyl, $(C_2-C_{10})$alkynyl, $-O-(C_1-C_{10})$alkyl, $-C(O)-O-(C_1-C_{10})$alkyl, aryl, and heteroaryl. For example, $R^1$ can be $-O-(C_1-C_{10})$alkyl (e.g., $OCH_3$). In some embodiments, $R^2$ is $-O-(C_1-C_{10})$alkyl (e.g., $OCH_3$). For example, a compound of Formula (1) can be chosen from:

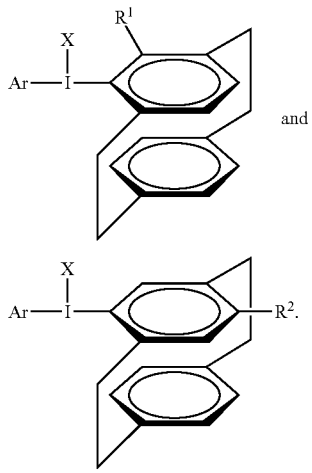

In some embodiments, one or more of $R^2$-$R^7$ is $(L)_p$-Z. L and Z can be covalently or noncovalently bound to one another.

The compounds described herein can be used with a variety of aryl and heteroaryl ring systems. In some embodiments, Ar is an electron rich aryl or heteroaryl ring system, for example, Ar—H can be more easily oxidized than benzene. In some embodiments, Ar is chosen from a phenylalanine derivative, tyrosine derivative, typtophan derivative, histidine derivative, and estradiol derivative. The Ar moiety can be present as a racemic mixture, enantiomerically pure, or as a mixture thereof. In some embodiments, the Ar moiety is enantiomerically enriched. For example, the Ar moiety can be present in an enantiomeric excess of at least 75%, an enantiomeric excess of at least 95%, or an enantiomeric excess of at least 98%.

In some embodiments, Ar can be selected from the group consisting of:

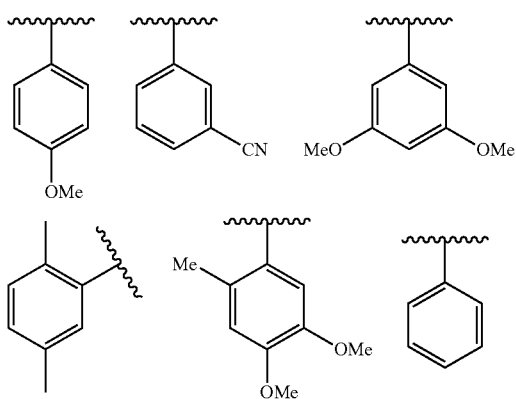

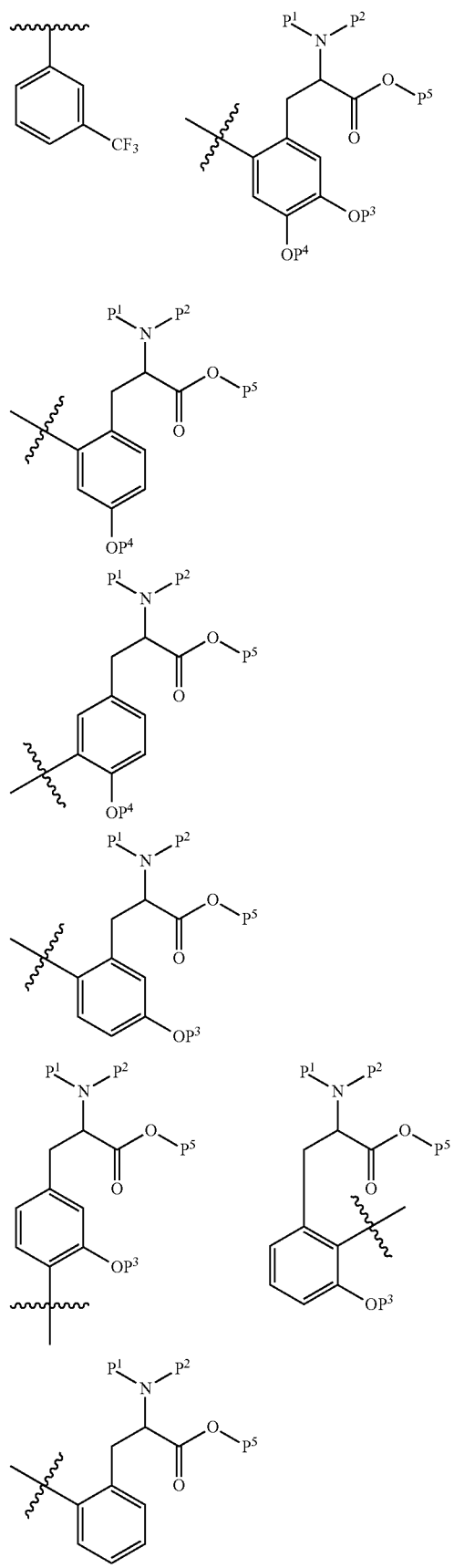

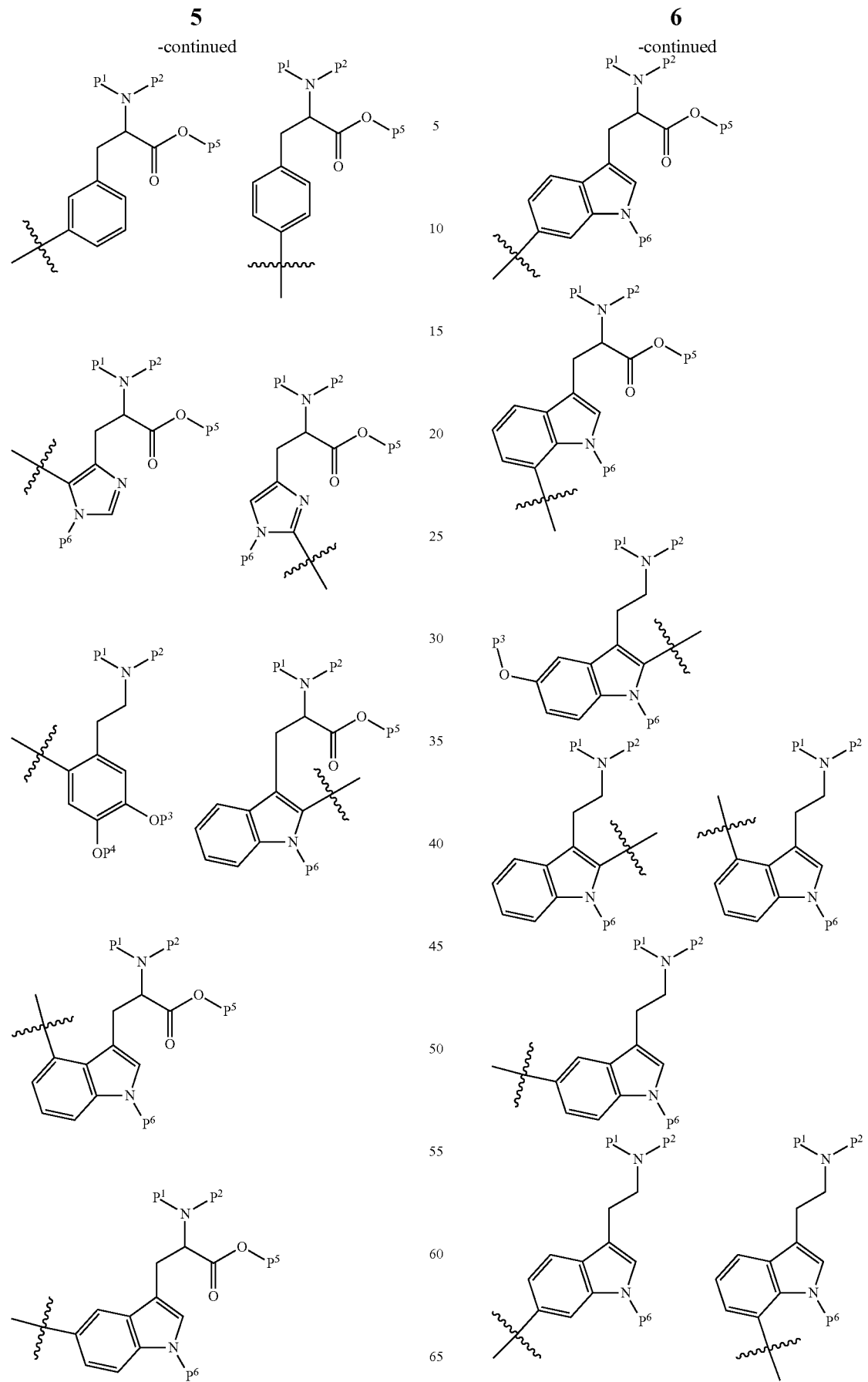

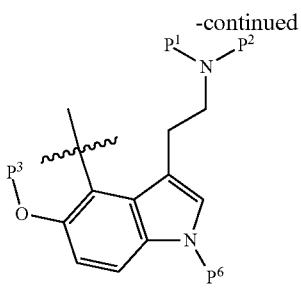
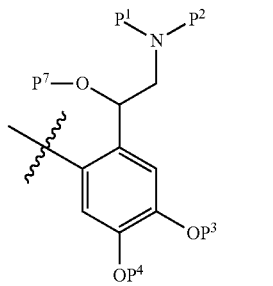
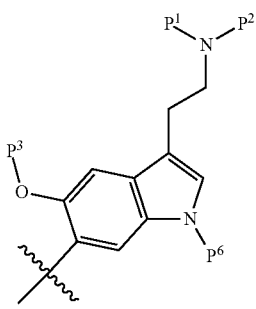
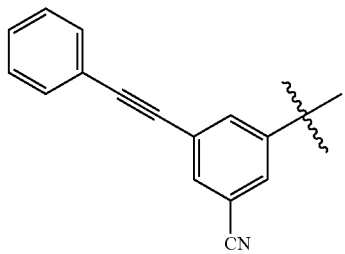
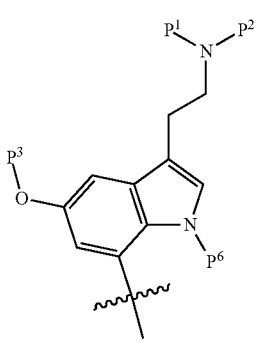
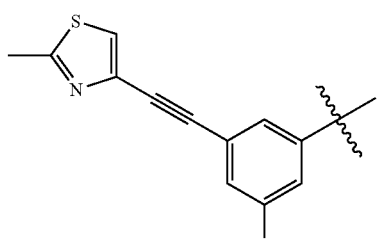
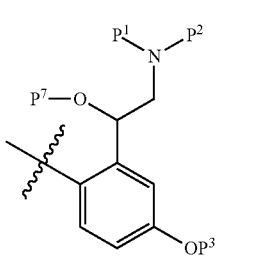
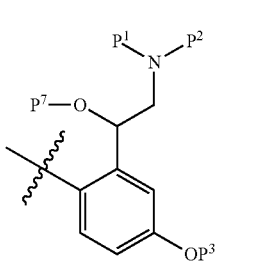
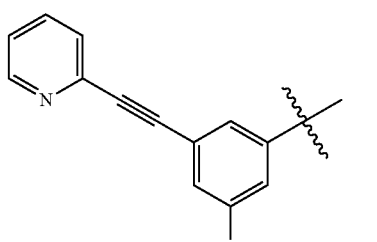
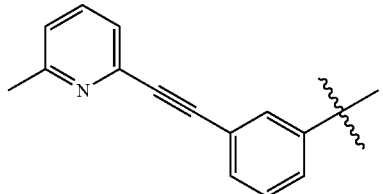
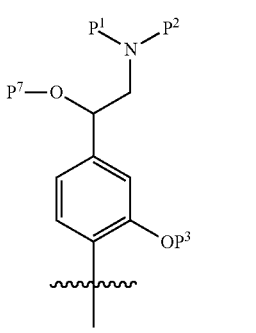
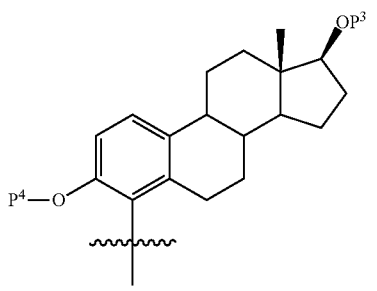

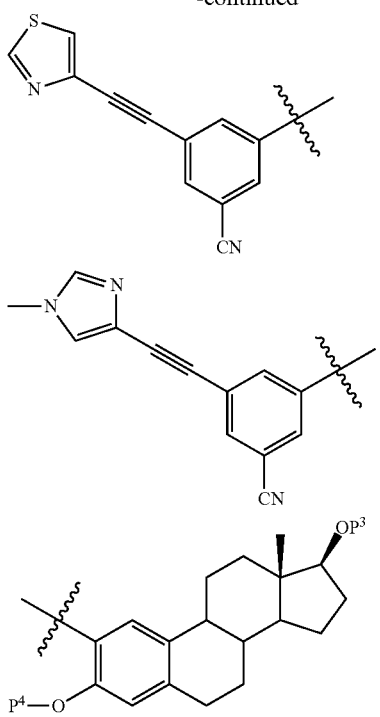

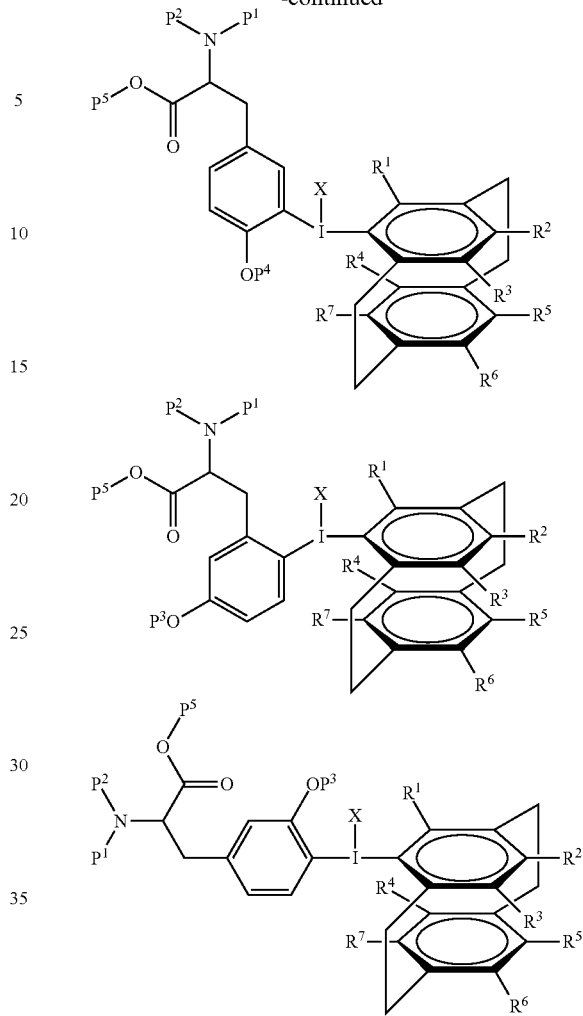

wherein:
- each of $P^1$ and $P^2$ are independently a nitrogen protecting group, or $P^1$ and $P^2$ come together to form a single nitrogen protecting group;
- each of $P^3$, and $P^4$ are independently an alcohol protecting group, or $P^3$ and $P^4$ come together to form a single oxygen protecting group; and
- $P^5$ is a carboxylic acid protecting group.

In some embodiments, the compound of Formula (1) is chosen from:

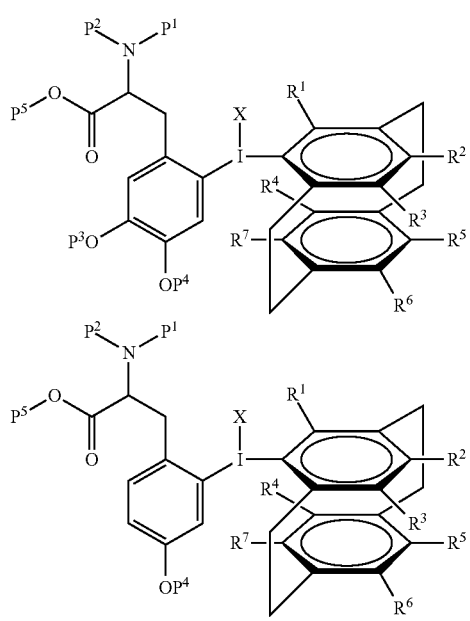

wherein:
- each of $P^1$ and $P^2$ are independently a nitrogen protecting group, or $P^1$ and $P^2$ come together to form a single nitrogen protecting group;
- each of $P^3$, and $P^4$ are independently an alcohol protecting group, or $P^3$ and $P^4$ come together to form a single oxygen protecting group; and
- $P^5$ is a carboxylic acid protecting group.

In some embodiments, the compound of Formula (1) is selected from the group consisting of:

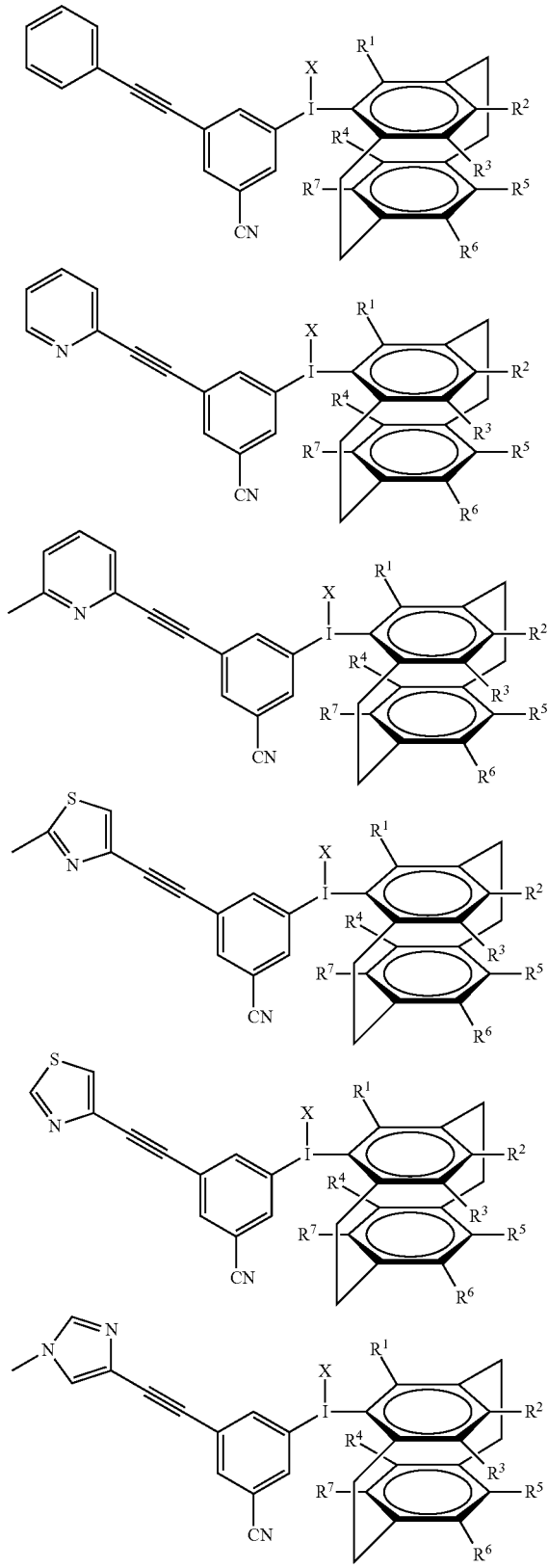

In some embodiments, the compound of Formula (1) is selected from the group consisting of:

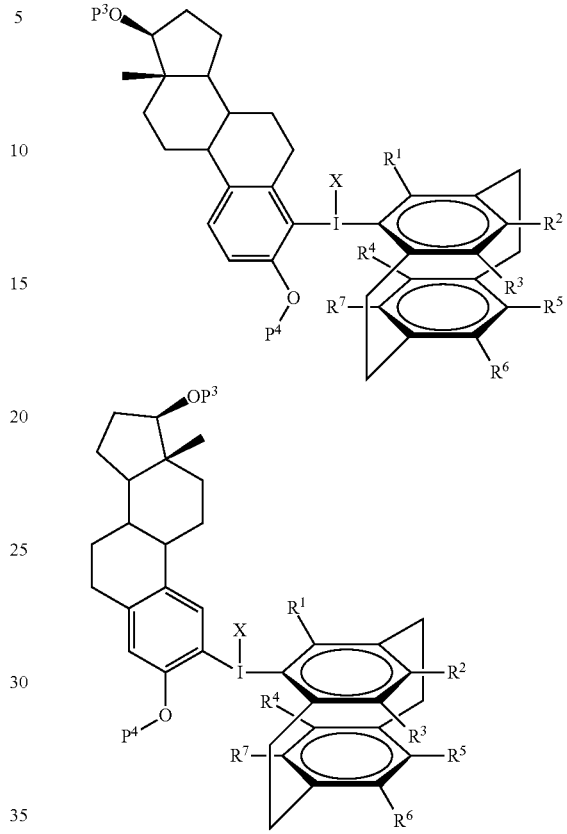

wherein:
each of $P^3$ and $P^4$ are independently an alcohol protecting group.

In any of the above embodiments, X can be F. For example, X can be $^{18}F$.

In some embodiments, a compound of Formula (1) can be a compound of Formula (3):

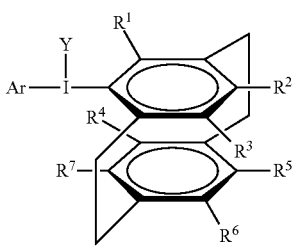

wherein Y is a leaving group. For example, Y can be selected from the group consisting of: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, chloride, bromide, and iodide.

Further provided herein is a method of making a compound of Formula (2):

Ar—X or

Formula (5):

Ar—F wherein Ar is a substituted or unsubstituted aryl or heteroaryl ring system; and X is a moiety whether the pKa of the acid H—X is less than 12, as described above. The method includes heating a solution comprising a compound MX (e.g., MF), wherein M is a counter ion and X is as defined above, and a compound of Formula (3).

In some embodiments, the solution comprising MX or MF and a compound of Formula (3) can further include a non-polar solvent. The non-polar solvent can be, for example, benzene, toluene, o-xylene, m-xylene, p-xylene, ethyl benzene, carbon tetrachloride, hexane, cyclohexane, fluorobenzene, chlorobenzene, nitrobenzene, or mixtures thereof. In some embodiments, the solution comprising MX or MF and a compound of Formula (3) can further include a polar solvent. The polar solvent can be, for example, acetonitrile, acetone, dichloromethane, ethyl acetate, tetrahydrofuran, dimethylformamide, 1,2-difluorobenzene, benzotrifluoride, or mixtures thereof.

In some embodiments, the method further comprises filtering the solution to remove insoluble material prior to heating. In some cases, the solvent is removed from the filtrate prior to heating. In some embodiments, the method further comprises removing salt by chromatography prior to heating (for example, removing salt using gel permeation chromatography).

Heating of the solution can be done at a temperature ranging from about 25° C. to about 250° C. In some embodiments, the heating occurs for from about 1 second to about 25 minutes. Heating can be accomplished by any reasonable method, for example, by a flash pyrolysis method, a conventional heating method, or by a microwave method.

Non-limiting examples of a compound of Formula (2) or (5) include:

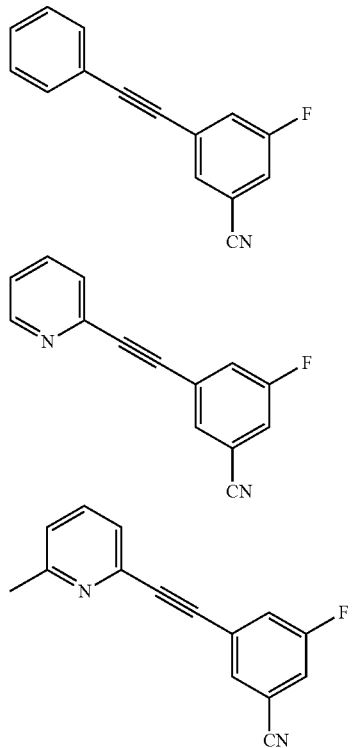

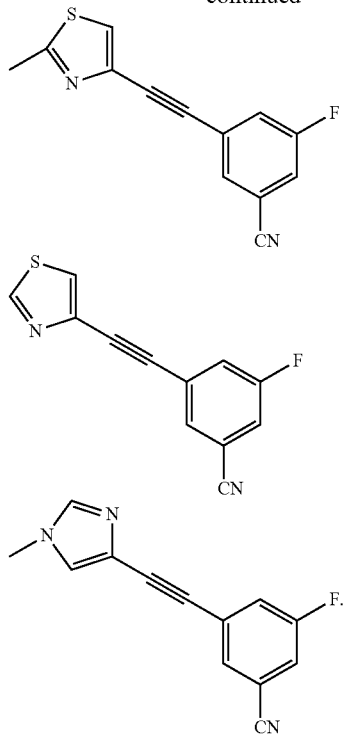

In some embodiments, the compound of Formula (2) or (5) can be chosen from:

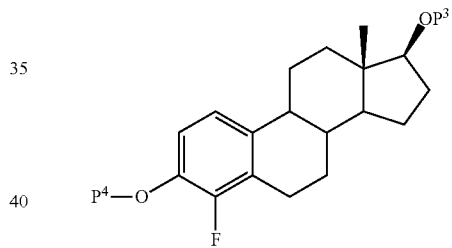

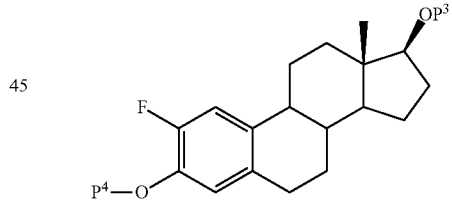

wherein:
each of $P^3$ and $P^4$ are independently an alcohol protecting group.

In some embodiments, the compound of Formula (2) or (5) is:

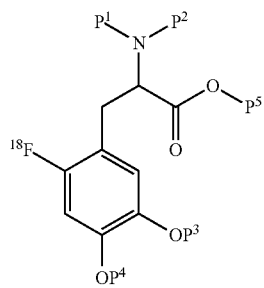

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.
For example, the compound can be:

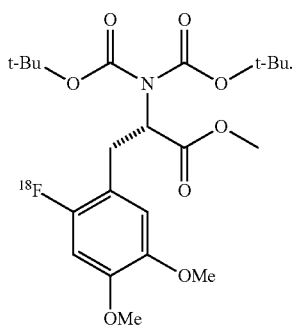 [SMILES: COC(=O)[C@H](Cc1cc(OC)c(OC)cc1[18F])N(C(=O)OC(C)(C)C)C(=O)OC(C)(C)C]

In some embodiments, the compound of formula (2) or (5) is:

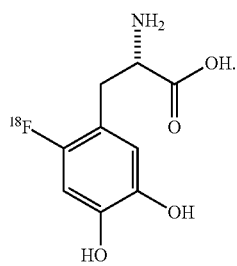

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

These and other features, aspects and advantages of the present teachings will become better understood with reference to the following description, examples and appended claims.

DESCRIPTION OF DRAWINGS

FIG. 1 shows the calculated transition state structures and activation barriers for a (2,5-dimethylphenyl) and [2.2]paracyclophan-4-yl iodonium salt.

DETAILED DESCRIPTION

Provided herein are methods of preparing substituted aryl and heteroaryl ring systems using iodonium cyclophane compounds and intermediates. For example, iodonium cyclophane salts and iodonium cyclophane fluorides, as provided herein, can undergo decomposition to prepare an aryl fluoride. In the thermal decomposition of unsymmetrial diaryliodonium salts, the identity of the aryl iodide reductively eliminated it typically dictated by electronic effects; for example, the electron-rich aryl iodide and the functionalized electron-poor aromatic compound are formed predominantly (see, for example, WO 2010/048170, which is incorporated by reference herein). This disclosure provides universal "locked" aryl substituents that result in StereoElectronic Control of Unidirectional Reductive Elimination (SECURE) from diaryliodonium salts. Since electronic effects cannot be used exclusively to achieve this end, steric and/or stereoelectronic effects can be exploited to gain regiocontrol of reductive elimination.

DEFINITIONS

As used herein, the singular forms "a," "an," and "the" include plural referents unless the context clearly dictates otherwise.

In general, the term "aryl" includes groups having at least 5 carbon atoms which form a ring structure and have an aromatic character, including 5- and 6-membered single-ring aromatic groups, such as benzene and phenyl. Furthermore, the term "aryl" includes polycyclic aryl groups, e.g., tricyclic, bicyclic, such as naphthalene and anthracene.

The term "heteroaryl" includes groups having at least 5 atoms which form a ring structure and have an aromatic character, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes polycyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indazole, or indolizine.

The term "substituted" means that an atom or group of atoms formally replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position.

The compounds provided herein may encompass various stereochemical forms and tautomers. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

As used herein, chemical structures which contain one or more stereocenters depicted with bold and dashed bonds, i.e., ⋮ | are meant to indicate absolute stereochemistry of the stereocenter(s) present in the chemical structure. As used herein, bonds symbolized by a simple line do not indicate a stereopreference. Unless otherwise indicated to the contrary, chemical structures, which include one or more stereocenters, illustrated herein without indicating absolute or relative stereochemistry encompass all possible steroisomeric forms of the compound (e.g., diastereomers, enantiomers) and mixtures thereof Structures with a single bold or dashed line, and at least one additional simple line, encompass a single enantiomeric series of all possible diastereomers.

The term "optically enriched" or "enantiomerically enriched" as used herein refers to the presence of an enantiomeric excess of either an R or an S isomer at a given stereocenter of a molecule in a composition. "Enantiomeric excess" is defined as |F(R)−F(S)| for a mixture of (R) and (S) enantiomers, with the composition given as the mole fractions F(R) and F(S), where F(R)+F(S)=1. The percent enantiomeric excess is given by 100|F(R)−F(S)|). Enantiomeric excess is frequently abbreviated as ee. In some embodiments, the ee for each species of a genus is independent of the other members of the genus.

The term "electron rich", as used herein, refers to an aryl or heteroaryl ring system which is more easily oxidized than benzene. For example the aryl or heteroaryl ring system may be substituted with one or more substituents having a Hammett $\sigma_p$ value of less than zero.

The term "fluorine", unless explicitly stated otherwise, includes all fluorine isotopes. Multiple fluorine isotopes are known, however, only $^{19}F$ is stable. The radioisotope $^{18}F$ has a half-life of 109.8 minutes and emits positrons during radioactive decay. The relative amount of $^{18}F$ present at a designated site in a compound of this disclosure will depend upon a number of factors including the isotopic purity of $^{18}F$ labeled reagents used to make the compound, the efficiency of incorporation of $^{18}F$ in the various synthesis steps used to prepare the compound, and the length of time since the $^{18}F$ has been produced. When a position is designated specifically as $^{18}F$ in the methods and compounds of the present disclosure, the position is understood to have at least about 0.01%, at least about 0.1%, at least about 1%, at least about 2%, at least about 3%, at least about 4%, at least about 5%, at least about 10%, at least about 15%, at least about 20%, at least about 25%, at least about 30%, at least about 35%, at least about 45%, at least about 50%, at least about 55%, at least about 60%, at least about 65%, at least about 70%, at least about 75%, at least about 80%, or at least about 85% $^{18}F$ incorporation at that site.

Compounds

Provided herein are aryl ligands on iodine that can generate a highly strained reductive elimination transition state. This strained transition state is created through the introduction of significant steric congestion above and/or below the aromatic ring in conjunction with little steric congestion in the plane of the ring. On such ligand is [n.n]cyclophane. Cyclophanes, as described herein, are a hydrocarbon consisting of an aromatic unit (e.g., a benzene ring) and an aliphatic chain that forms a bridge between two non-adjacent positions of the aromatic ring. For example, [2.2]paracyclophane iodine(III) salts are described herein, but those of skill in the art will appreciate that other cyclophanes, e.g., [2.2]metacyclophane or [2.2]orthocyclophane, can also be used in the compounds and methods described herein. In addition, cyclophanes are chiral and the cyclophane moieties provided herein may be enantiomerically pure, racemic, or a mixture thereof.

One example of a [2.2]paracyclophane iodine(III) salt is a compound of Formula (1)

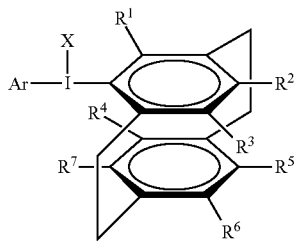

wherein:

Ar is a substituted or unsubstituted aryl or heteroaryl ring system;

X is either a moiety wherein the pKa of the acid H—X is less than 12 or a leaving group;

$R^1$ is hydrogen or a substituent having a Hammett $\sigma_p$ value of less than zero; and $R^2, R^3, R^4, R^5, R^6$, and $R^7$ are independently selected from the group consisting of: H, $CF_3$, $OCF_3$, CN, hydroxyl, amino, aminoalkyl, $(CH_2)_nN(CH_2)_m$, —$SR^8$, —$SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_n NR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, and $(L)_p$-Z, or one or more of $R^2$ and $R^3$, $R^4$ and $R^7$, and $R^5$ and $R^6$ come together to form a fused cycloalkyl, heterocycloalkyl, aryl, or heteroaryl ring system;

each m, n, and p are independently an integer from 0 to 10;

each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

L is a linker; and

Z is a solid support.

The X moiety can be selected from atoms and compounds in which the pKa of the acid H—X (i.e., the conjugate acid of X) is less than about 12. In some cases, X comprises a radioactive isotope (e.g., $^{18}F$, $^{123}I$, $^{131}I$, $^{32}P$, and $^{33}P$). In some embodiments, X can be chosen from halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, X can be fluoride, chloride, bromide, iodide, trifluoroacetate, benzoate, and acetate. In some embodiments, X is fluoride. In some embodiments, X is a radioactive isotope of fluoride ($^{18}F$).

X can also be any suitable leaving group. In some embodiments, X is a weakly coordinating anion (i.e., an anion that coordinates only weakly with iodine). For example, X can be the conjugate base of a strong acid, for example, any anion for which the pKa of the conjugate acid (H—X) is less than about 1. For example, X can be triflate, mesylate, nonaflate, hexaflate, toluene sulfonate(tosylate), nitrophenyl sulfonate (nosylate), bromophenyl sulfonate(brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, chloride, bromide, or iodide. In some embodiments, a slightly more basic leaving group such as acetate or benzoate may be used.

The aryl rings that form the cyclophane moeity may be substituted or unsubstituted as described above. In some embodiments, at least one aryl ring is substituted with at least one substituent having a Hammett $\sigma_p$ value of less than zero (see, for example, "A survey of Hammett substituent constants and resonance and field parameters", Corwin. Hansch, A. Leo, R. W. Taft *Chem. Rev.*, 1991, 91 (2), pp 165-195). For example, $R^1$ can be selected from —$(C_1-C_{10})$alkyl, $(C_2-C_{10})$alkenyl, $(C_2-C_{10})$alkynyl, —C(O)—O—$(C_1-C_{10})$alkyl, aryl, and heteroaryl. In some embodiments, $R^1$ can be —O—($C_1$-$C_{10}$)alkyl, for example, $R^1$ can be $OCH_3$. Similarly, in some embodiments, $R^2$ can be —O—($C_1$-$C_{10}$)alkyl, for example, $R^2$ can be $OCH_3$. For example, the compound of Formula (1) can be a compound of Formula (1A) or (1B):

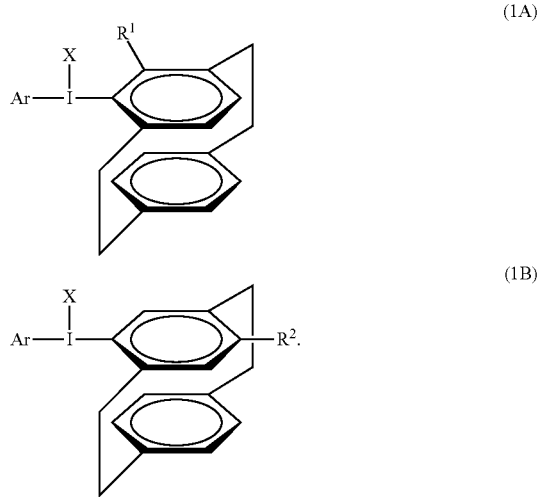

In some embodiments, adjacent R moieties (e.g., $R^2$ and $R^3$, $R^4$ and $R^7$, and/or $R^5$ and $R^6$) can come together to form a fused cycloalkyl, heterocycloalkyl, aryl, or heteroaryl ring system. For example, the cyclophane can include substituted or unsubstituted napthyl or anthracyl rings as the upper and/or lower aromatic ring moieties.

In some cases, the cyclophane ligand can be substituted with a solid support, Z. A "solid support" may be any suitable solid-phase support which is insoluble in any solvents to be used but which can be covalently or noncovalently bound (e.g., to the cyclophane ligand or to an optional linker). Examples of suitable solid supports include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a reaction vessel, for example a cartridge or a microfabricated vessel. See, for example, U.S. 2007/0092441. In some embodiments, the supports can be sealed into HPLC columns.

In some embodiments, the solid support is covalently or noncovalently bound to the cyclophane ligand through the use of a linker, L. A "linker" can be any suitable organic group which serves to space the ligand from the solid support structure so as to maximize reactivity. In some embodiments, L and Z are covalently bound to one another. For example, a linker can include a $C_{1-20}$ alkyl or a $C_{1-20}$ alkoxy, attached to the solid support, for example, a resin can be linked by an amide ether or a sulphonamide bond. The linker may also be a polyethylene glycol (PEG) linker. Examples of such linkers are well known to those skilled in the art of solid-phase chemistry. In some cases the linker and solid support are noncovalently bound to one another. Examples of noncovalent means for conjugation of a linker and a solid support include, e.g., ionic bonding, hydrophobic interactions, ligand-nucleotide binding, chelating agent/metal ion pairs or specific binding pairs such as avidin/biotin, streptavidin/biotin, anti-fluorescein/fluorescein, anti-2,4-dinitrophenol (DNP)/DNP, anti-peroxidase/peroxidase, anti-digoxigenin/digoxigenin or, more generally, receptor/ligand.

In some embodiments, a fluorous tag ($C_nF_{(2n+1)}$) can be used as a linker to immobilize a compound of Formula (1) on a fluorous support. For example, such immobilization can be accomplished by using a fluorophobic solvent such as acetonitrile. Examples of fluorous supports include powdered polyfluorinated resins (PTFE or PFA (DuPont)) or heavily fluorinated silica gels (FluoroFlash (Fluorous Technologies)). In some embodiments, a linker can comprise a fluorous alcohol as the source of the tag. This tag can be linked to the cyclophane ligand through any suitable organic linkage, for example, an alkyl group, polyethylene glycol (PEG) ethers, or mixtures of aliphatic, aromatic, and PEG linkers. In some embodiments, the length of the perfluoroalkyl chain on the linker can range from $C_6F_{13}$ to $C_{20}F_{41}$. In addition, multiple fluorous tags may be incorporated into the same iodonium salt.

The compounds described herein can be used with a variety of aryl and heteroaryl ring systems. Accordingly, the Ar moiety can be any aryl or heteroaryl ring system in which substitution by X (e.g., F such as $^{18}F$) is desired. In some embodiments, the Ar moiety is enantiomerically enriched. For example, the Ar moiety can be present in an enantiomeric excess of at least 75%, at least 95%, or at least 98%. In some embodiments, Ar is enantiomerically pure.

Ar can be an electron rich aryl or heteroaryl ring system, such as a ring system where Ar—H is more easily oxidized than benzene. In some embodiments, Ar is chosen from a phenylalanine derivative, tyrosine derivative, typtophan derivative, histidine derivative, and estradiol derivative.

In some embodiments, Ar can be selected from the group consisting of:

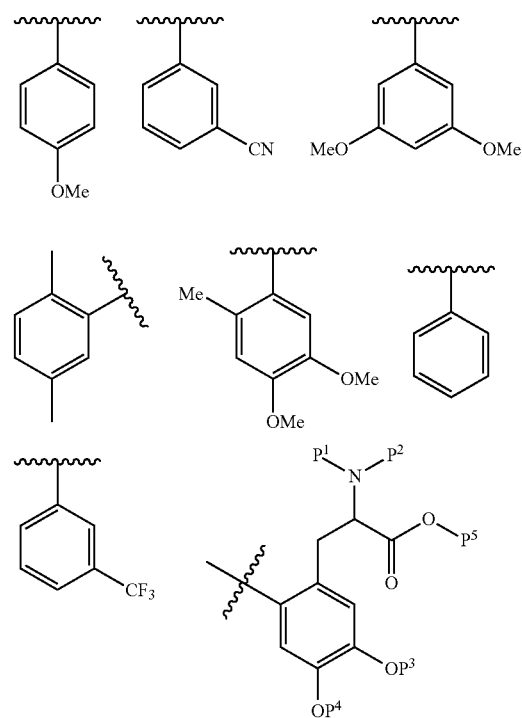

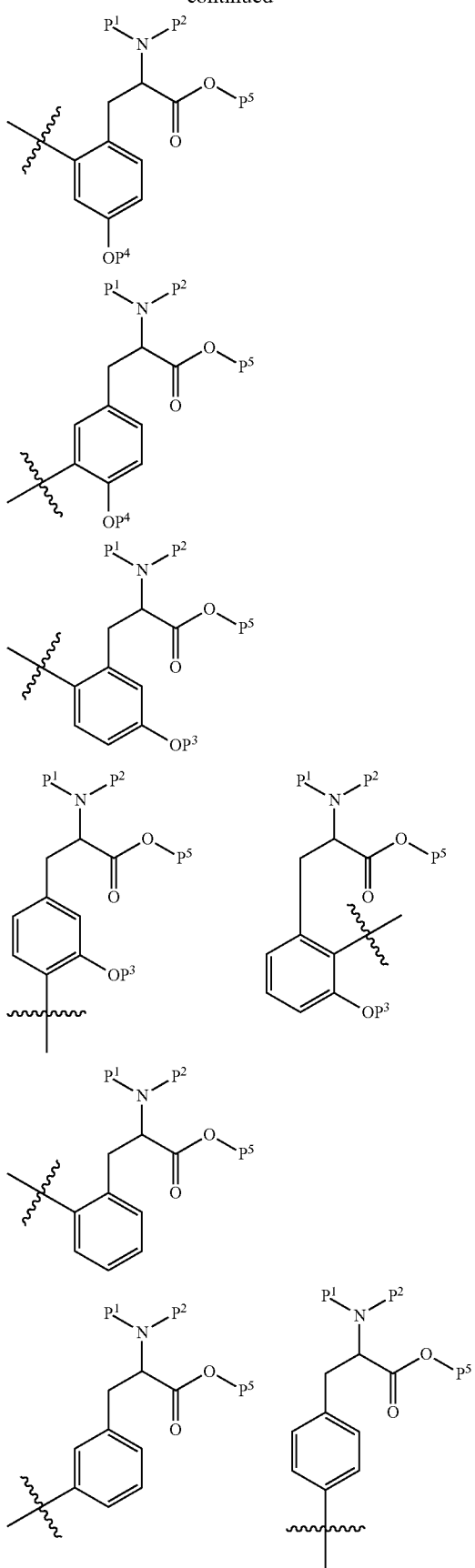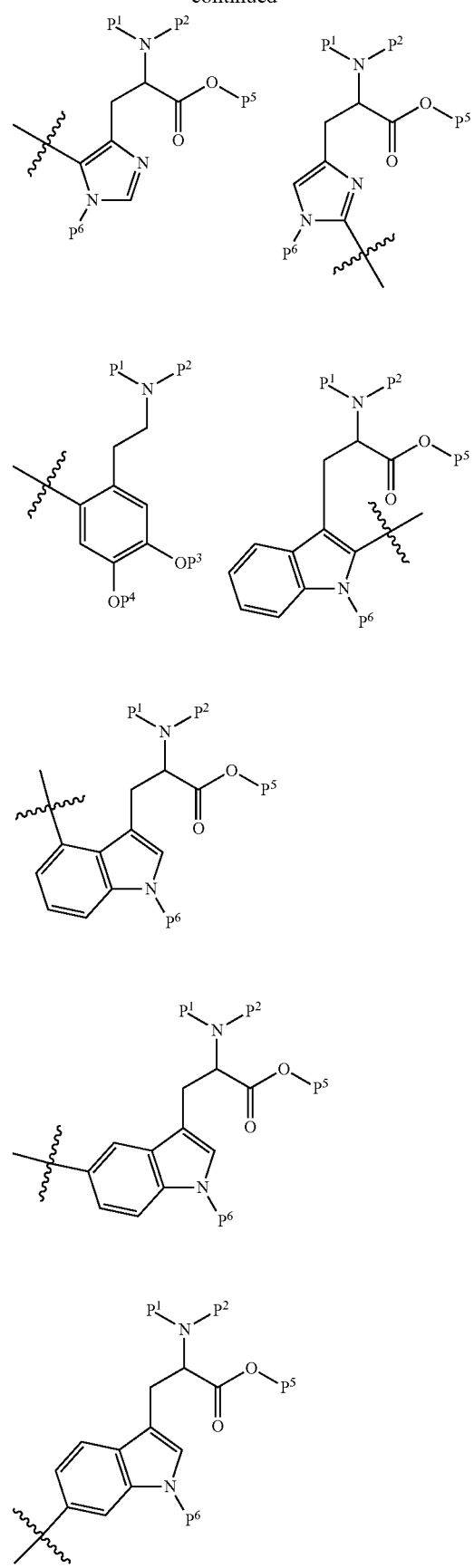

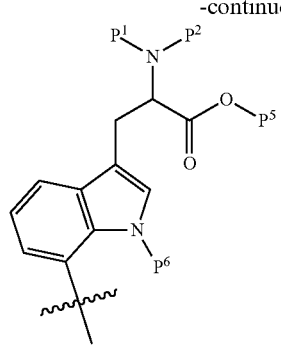
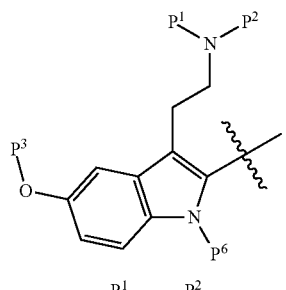
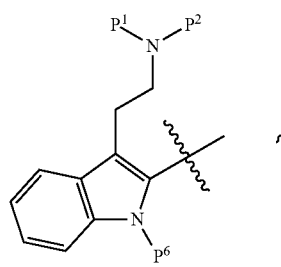
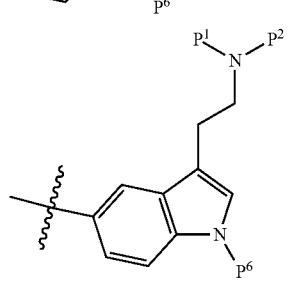
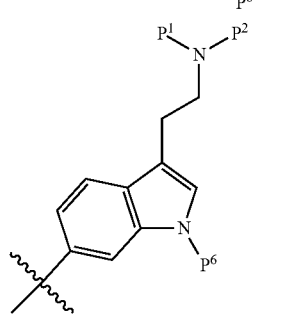
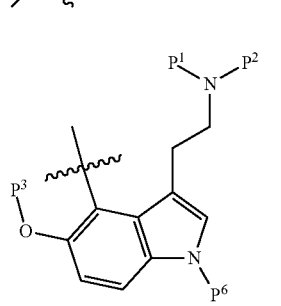
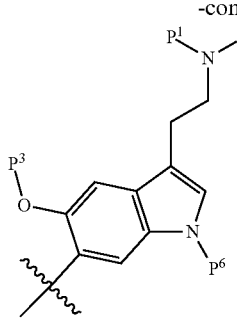
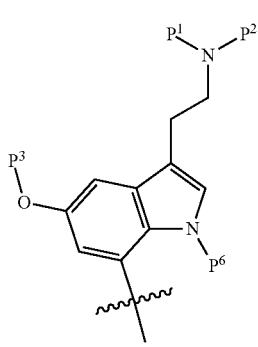
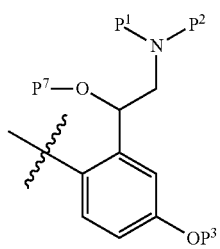
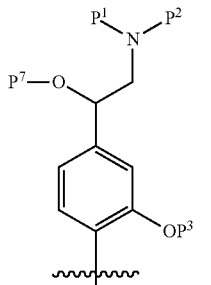
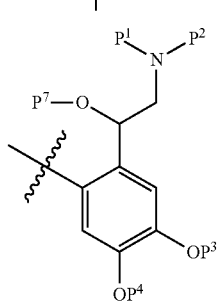

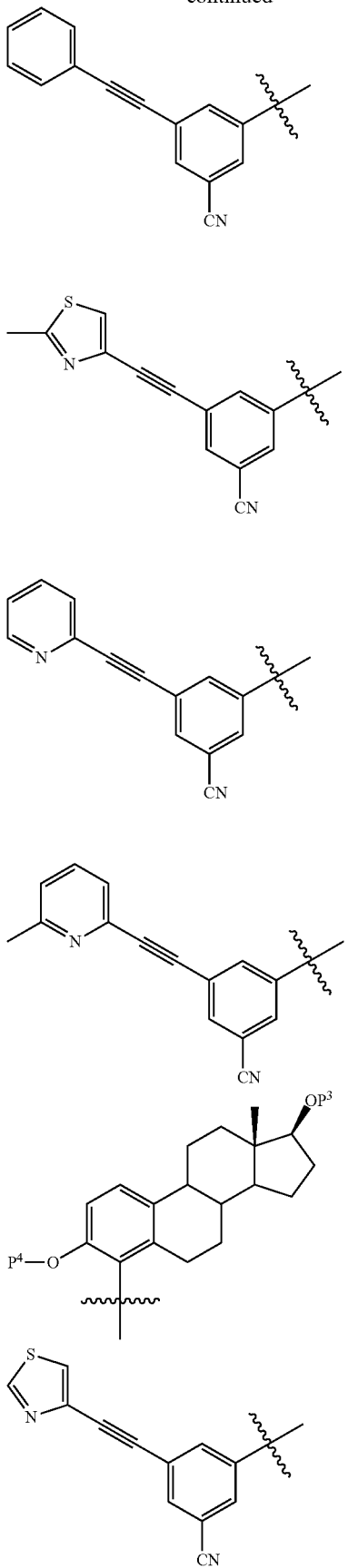

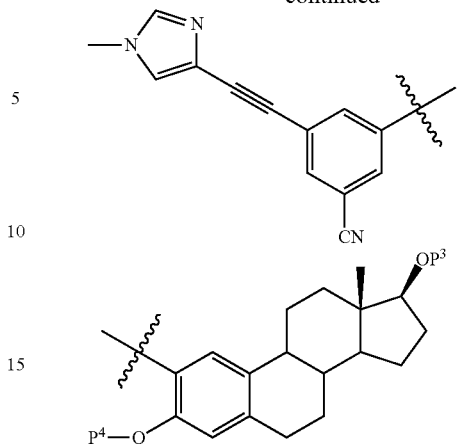

wherein:

each of $P^1$, $P^2$ and $P^6$ are independently a nitrogen protecting group, or $P^1$ and $P^2$ come together to form a single nitrogen protecting group;

each of $P^3$, $P^4$, and $P^7$ are independently an alcohol protecting group, or $P^3$ and $P^4$ come together to form a single oxygen protecting group; and $P^5$ is a carboxylic acid protecting group.

Protecting groups as described herein can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W.; Wuts, P. G. M. *Protective Groups in Organic Synthesis,* 2.sup.nd ed.; Wiley: N.Y., 1991).

A nitrogen protecting group can be any temporary substituent which protects an amine moiety from undesired chemical transformations. Examples of such protecting groups include, but are not limited to allylamine, benzylamines (e.g., bezylamine, p-methoxybenzylamine, 2,4-dimethoxybenzylamine, and tritylamine), acetylamide, trichloroacetammide, trifluoroacetamide, pent-4-enamide, phthalimides, carbamates (e.g., methyl carbamate, t-butyl carbamate, benzyl carbamate, allyl carbamates, 2,2,2-trichloroethyl carbamate, and 9-fluorenylmethyl carbamate), imines, and sulfonamides (e.g., benzene sulfonamide, p-toluenesulfonamide, and p-nitrobenzenesulfonamide).

An oxygen protecting group can be any temporary substituent which protects a hydroxyl moiety from undesired chemical transformations. Examples of such protecting groups include, but are not limited to esters (e.g., acetyl, t-butyl carbonyl, and benzoyl), benzyl (e.g., benzyl, p-methoxybenzyl, and 2,4-dimethoxybenzyl, and trityl), carbonates (e.g., methyl carbonate, allyl carbonate, 2,2,2-trichloroethyl carbonate and benzyl carbonate) ketals, and acetals, and ethers.

In some embodiments, the compound of Formula (1) can be selected from the group consisting of:

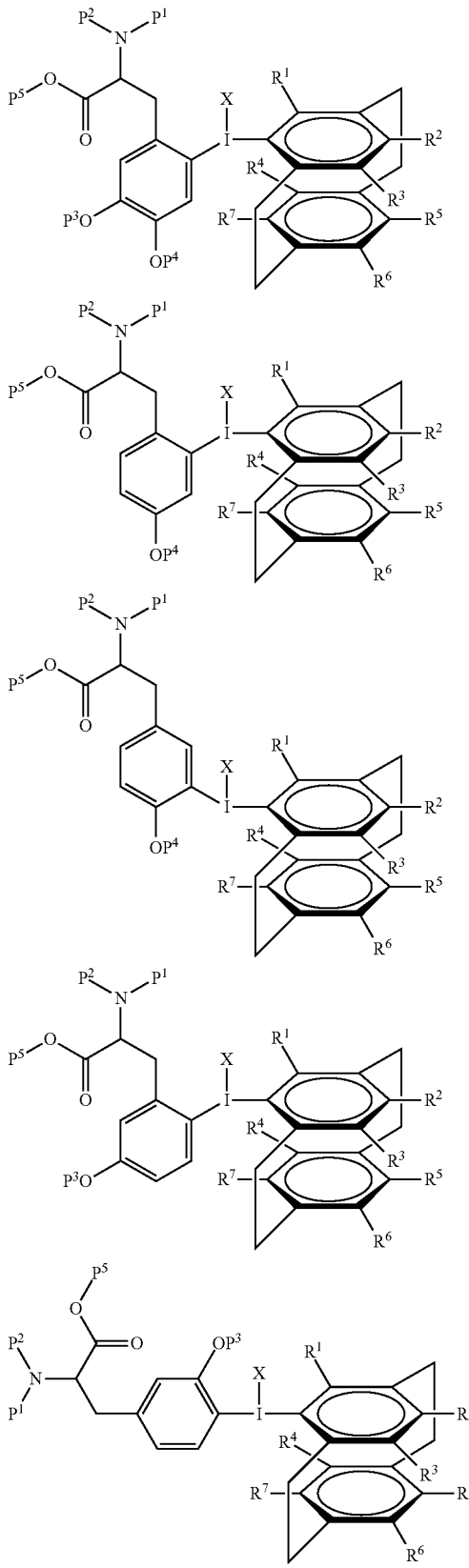

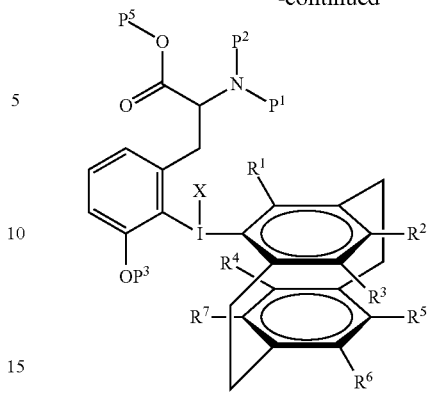

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

In some cases, the compound of Formula (1) is selected from the group consisting of:

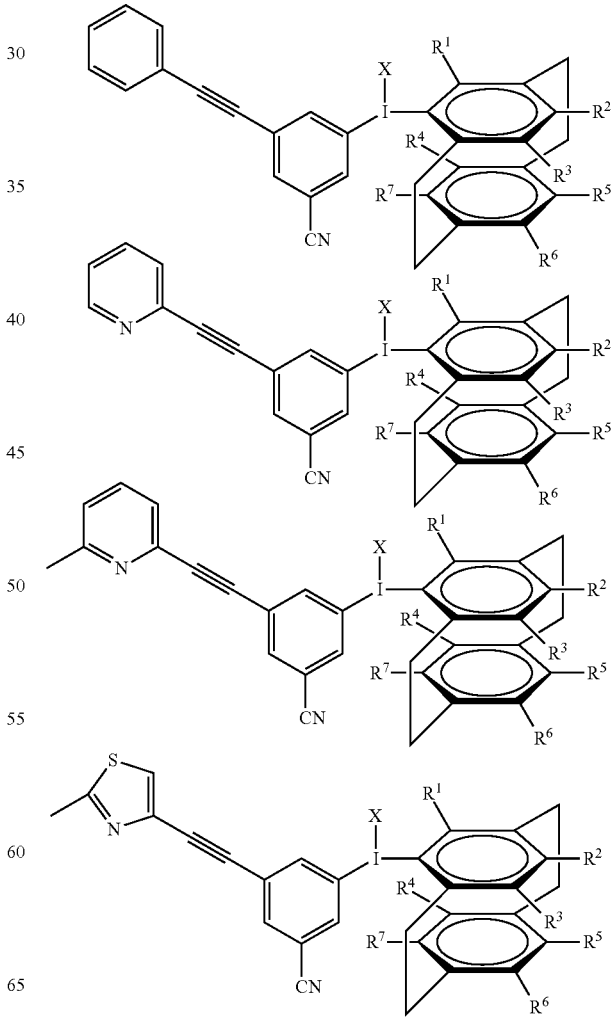

-continued

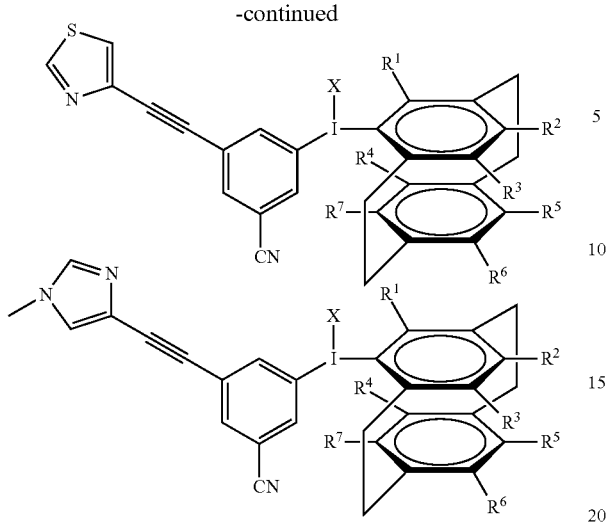

A compound of Formula (1) can also be selected from the group consisting of:

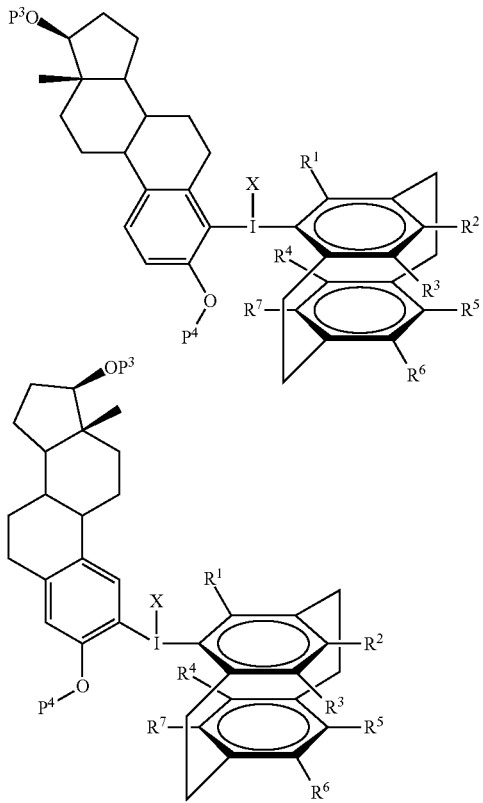

wherein:
each of $P^3$ and $P^4$ are independently an alcohol protecting group.

Also provided herein is a compound of Formula (4):

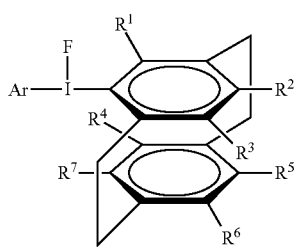

(4)

wherein Ar, $R^1$, $R^2$, $R^3$, $R^4$, $R^5$, $R^6$, and $R^7$ are as described above. For example, the compound of Formula (4) can be a compound of Formula (4A) or 4(B):

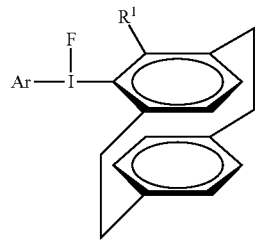

(4A)

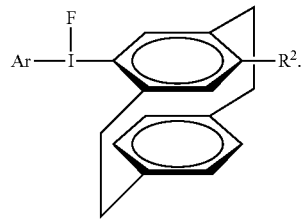

(4B)

In some embodiments, F is $^{18}F$.

The compound of Formula (4) can be selected from the group consisting of:

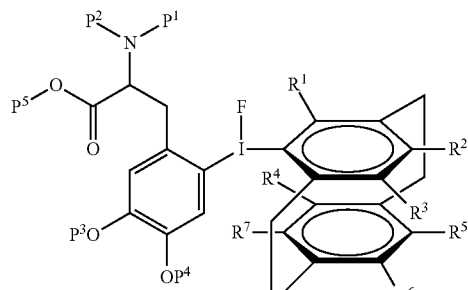

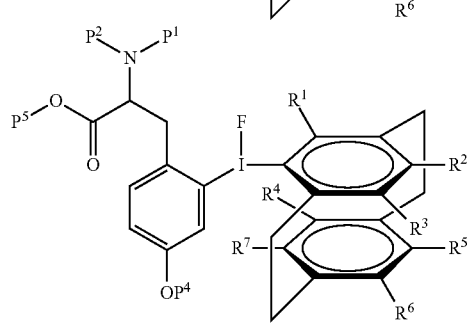

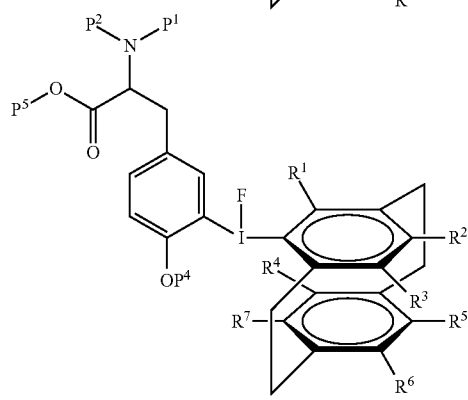

-continued

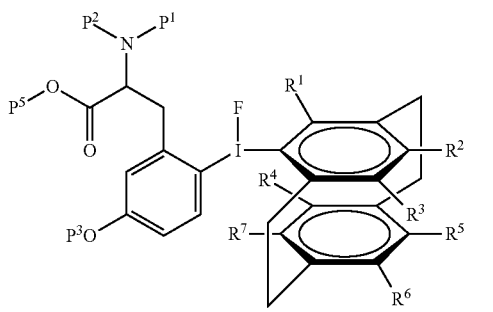

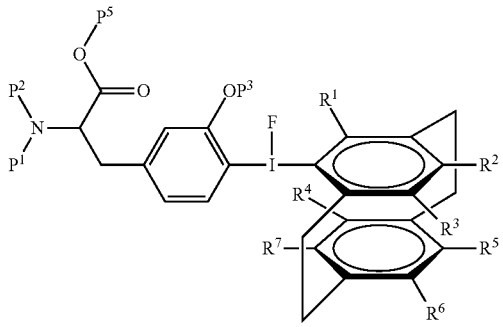

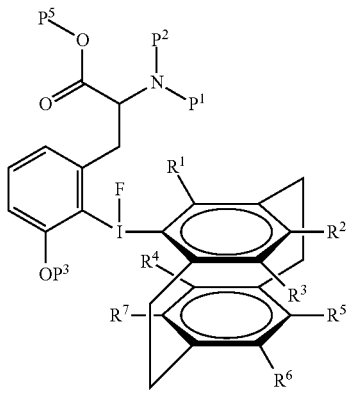

wherein:
each of P¹ and P² are independently a nitrogen protecting group, or P¹ and P² come together to form a single nitrogen protecting group;
each of P³, and P⁴ are independently an alcohol protecting group, or P³ and P⁴ come together to form a single oxygen protecting group; and
P⁵ is a carboxylic acid protecting group.

In some embodiments, the compound of Formula (4) is selected from the group consisting of:

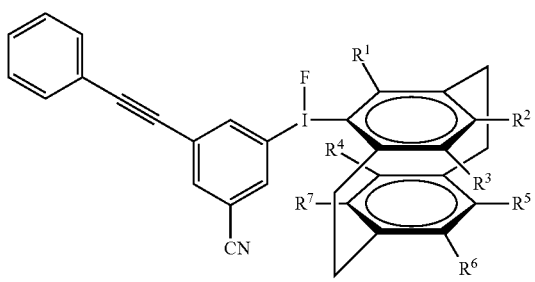

-continued

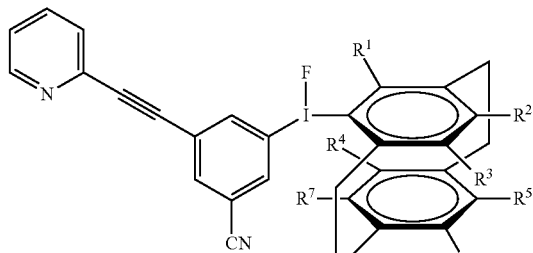

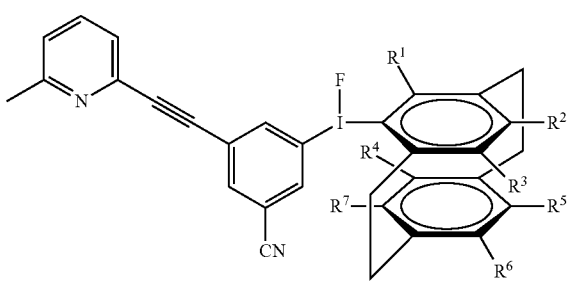

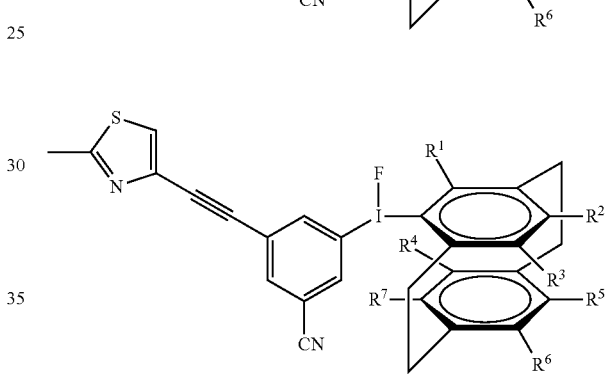

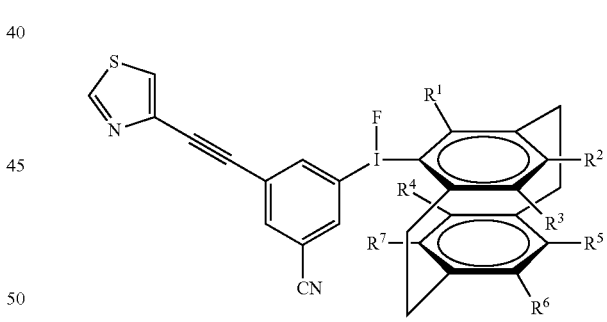

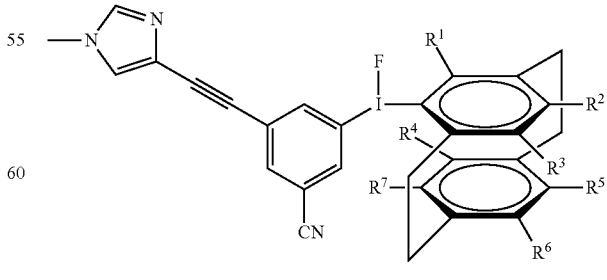

Also provided herein are compounds of Formula (4) selected from the group consisting of:

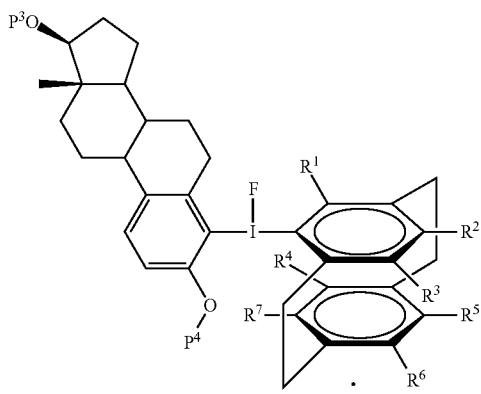

wherein:
each of $P^3$ and $P^4$ are independently an alcohol protecting group.

The iodonium cyclophane compounds described herein can be prepared from commercially available starting materials using various methods known to those of ordinary skill in the art. The method used for synthesizing the compounds will depend on the functionality present on the Ar moiety. Potentially reactive functional groups present on the Ar moiety can be masked using a protecting group prior to the synthesis of the iodonium cyclophane compound. The particular method employed for preparing the iodonium cyclophane compounds will be readily apparent to a person of ordinary skill in the art.

For compounds that bear sensitive functionality on the accepting group (Ar), organometallic reagents that feature more covalent (more stable) C-M bonds can be used. For example, organometallic compounds including tin, boron, and zinc. If there is no functional group incompatibility, more basic organometallic reagents (organolithium, Grignard, etc.) can be used to prepare the iodonium cyclophane salts.

In some embodiments, an unsymmetrical iodonium cyclophane salt can be prepared through the reaction of an arylzinc halide (e.g., arylzinc chloride). Arylzinc halide salts can be prepared by methods known by those of skill in the art. For example, 4-Bromo-[2.2]paracyclophane can be lithiated (e.g., using t-BuLi, Et$_2$O, −78° C.) and transmetalated with anhydrous zinc chloride to prepare an arylzinc chloride. This salt can then be reacted with an aryl iodonium salt (e.g., 2,5-dimethylphenyliodonium diacetate) at low temperature (e.g., −40° C.) to prepare a compound of Formula (I). Ion exchange or other method can be used to alter the nucleophile (e.g., X) as desired.

For example, a compound of Formula (1) can be made using the reaction shown in Scheme 1.

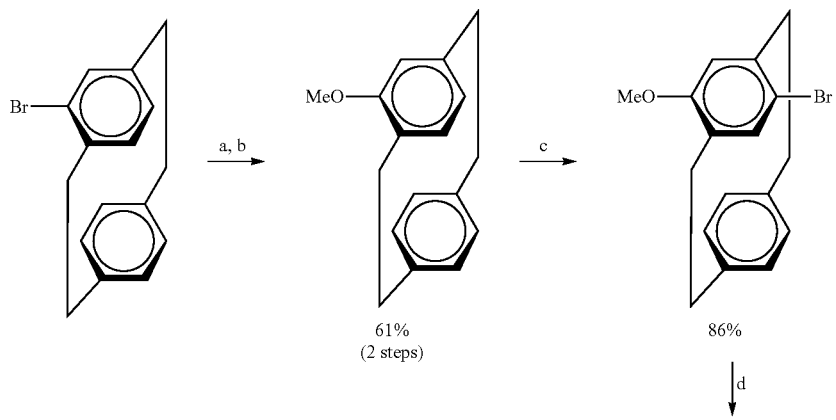

Scheme 1.

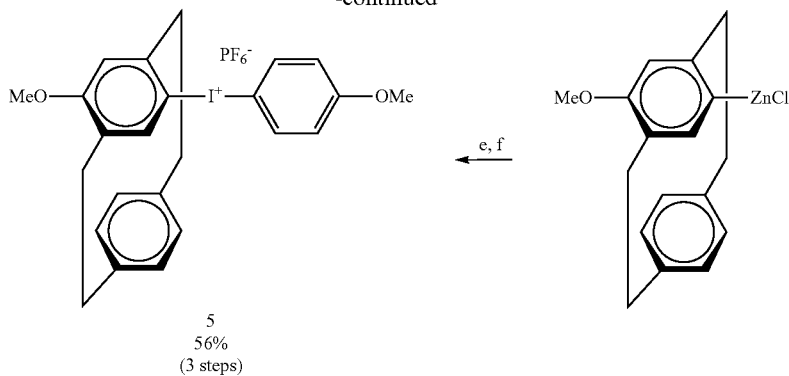

5
56%
(3 steps)

a. 1. t-BuLi, Et$_2$O, -78° C., 2. B(OMe)$_3$, 3. H$_2$O$_2$, NaOH, H$_2$O;
b. K$_2$CO$_3$, CH$_3$I, CH$_3$CN, 80° C.;
c. NBS, CH$_2$Cl$_2$;
d. 1. t-BuLi, Et$_2$O, -78° C., 2. ZnCl$_2$; and
e. 1. 4-MeOC$_6$H$_4$I(OAc)$_2$, CH$_3$CN, -40° C., f. NaPF$_6$, H$_2$O.

Additional examples are provided in the Examples section below.

Persons skilled in the art will be aware of variations of, and alternatives to, the processes described which allow the compounds defined herein to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the synthetic steps.

The skilled person will appreciate that the iodonium cyclophane compounds described could be made by methods other than those herein described, by adaptation of the methods herein described and/or adaptation of methods known in the art, for example US 2007/0092441, or using standard textbooks such as "Comprehensive Organic Transformations—A Guide to Functional Group Transformations", R C Larock, Wiley-VCH (1999 or later editions) and "Science of Synthesis", Volume 31a, 2007 (Houben-Weyl, Thieme)

Methods of Preparing Substituted Aryl and Heteroaryl Ring Systems

Provided herein are methods of preparing substituted aryl and heteroaryl ring systems using iodonium cyclophane compounds, salts, and intermediates. For example, iodonium cyclophane salts and iodonium cyclophane fluorides, as provided herein, can undergo decomposition to prepare an aryl fluoride.

For example, provided herein is a method of making a compound of Formula (2):

Ar—X wherein:

Ar is a substituted or unsubstituted aryl or heteroaryl ring system; and

X is a moiety wherein the pKa of the acid H—X is less than 12. In some embodiments, a compound of Formula (2) can be prepared as shown in Scheme 2.

Scheme 2.

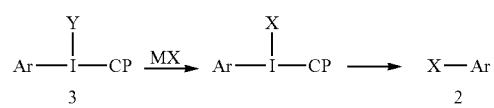

wherein CP is a cyclophane ligand as described herein.

In some embodiments, a compound of Formula (2) can be prepared by heating a solution having a compound MX, wherein M is a counter ion and X is as defined above, and a compound of Formula (3):

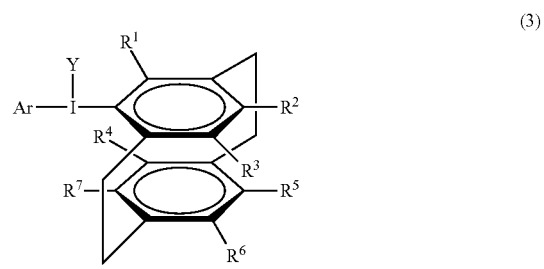

(3)

wherein:

Ar is a substituted or unsubstituted aryl or heteroaryl ring system as described above;

Y is a leaving group;

$R^1$ is hydrogen or a substituent having a Hammett $\sigma_p$ value of less than zero; and $R^2, R^3, R^4, R^5, R^6$, and $R^7$ are independently selected from the group consisting of: H, $CF_3$, $OCF_3$, CN, hydroxyl, amino, aminoalkyl, $(CH_2)_nN(CH_2)_m$, $-SR^8$, $-SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, and $(L)_p$-Z, or one or more of $R^2$ and $R^3$, $R^4$ and $R^7$, and $R^5$ and $R^6$ come together to form a fused cycloalkyl, heterocycloalkyl, aryl, or heteroaryl ring system;

each m, n, and p are independently an integer from 0 to 10;

each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

L is a linker; and

Z is a solid support.

Substituted aryls and heteroaryls which are prepared using the methods described herein can have an X moiety which includes any moiety in which the pKa of H—X (i.e., the conjugate acid of X) is less than about 12. In some cases, X comprises a radioactive isotope (e.g., $^{18}F$, $^{123}I$, $^{131}I$, $^{32}P$, and $^{33}P$). In some embodiments, X can be chosen from halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, X can be fluoride, chloride, bromide, iodide, trifluoroacetate, benzoate, and acetate. In some embodiments, X is fluoride. In some embodiments, X is a radioactive isotope of fluoride (e.g., $^{18}F$).

Y can be any suitable leaving group. In some embodiments, Y is a weakly coordinating anion (i.e., an anion that coordinates only weakly with iodine). For example, Y can be the conjugate base of a strong acid, for example, any anion for which the pKa of the conjugate acid (H—Y) is less than about 1. In some embodiments, Y is chosen from triflate, mesylate, nonaflate, hexaflate, toluene sulfonate(tosylate), nitrophenyl sulfonate(nosylate), bromophenyl sulfonate(brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, chloride, bromide, and iodide. In some embodiments, a slightly more basic leaving group such as acetate or benzoate may be used.

The counter ion M can be any suitable cation for the desired X. The choice of the source of X, and accordingly M, is readily within the knowledge of one of ordinary skill in the art. For example, M can be chosen from an alkali metal, alkaline earth metal and transition metal salts such as, for example, calcium, magnesium, potassium, sodium and zinc salts. Metal cations may also be complexed to cryptands or crown ethers to enhance their solubility and to labilize the X moiety. M can also include organic salts made from quaternized amines derived from, for example, N,N' dibenzylethylenediamine, chloroprocaine, choline, diethanolamine, ethylenediamine, meglumine (N-methylglucamine) and procaine. In some embodiments, M can be a lithium, sodium, potassium, or cesium with cryptands or crown ethers, a tetrasubstituted ammonium cation, or phosphonium cation. When X is fluoride, the choice of fluoride source is also readily within the knowledge of one of ordinary skill in the art. A variety of fluoride sources can be used in the preparation of the fluorinated aryl and heteroaryl compounds as provided herein, including but not limited to NaF, KF, CsF, tetrabutylammonium fluoride, and tetramethylammonium fluoride. In certain instances the choice of fluoride source will depend on the functionality present on the compound of Formula (3).

For the compounds of Formula (2) and (3), Ar, $R^1$, $R^2$, $R^3$, $R^4$, $R^5$, $R^6$, and $R^7$ can be as described above for the compounds of Formula (1) and (4). For example, a compound of Formula (3) can be a compound of Formula (3A) or a compound of Formula (3B)

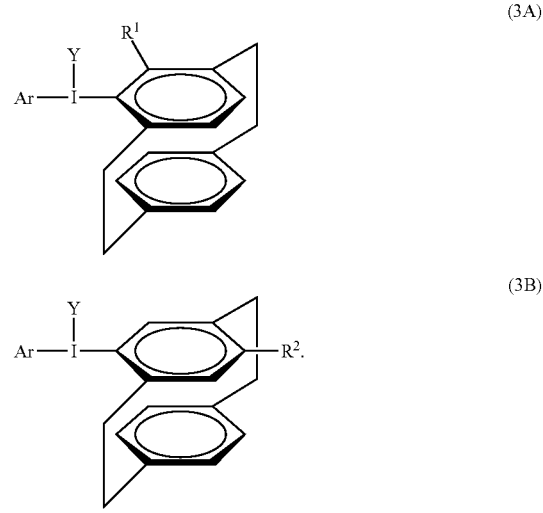

(3A)

(3B)

In some embodiments, the compound of Formula (3) is chosen from:

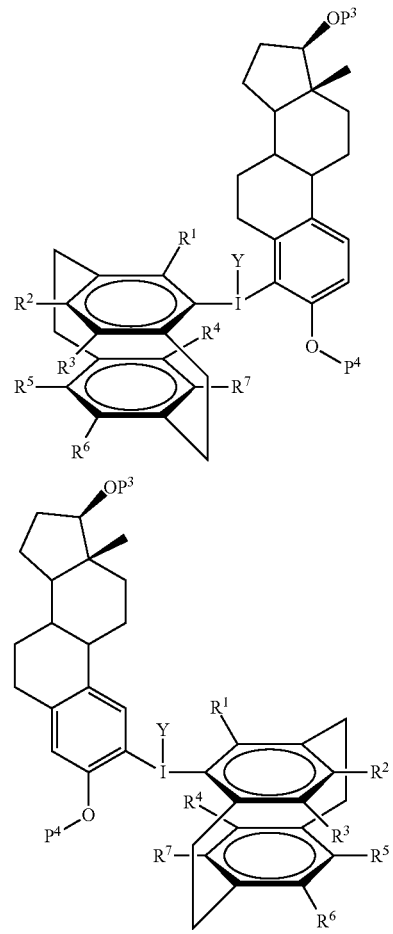

wherein each of $P^3$ and $P^4$ are independently an alcohol protecting group.

In some cases, the compound of Formula (3) is:

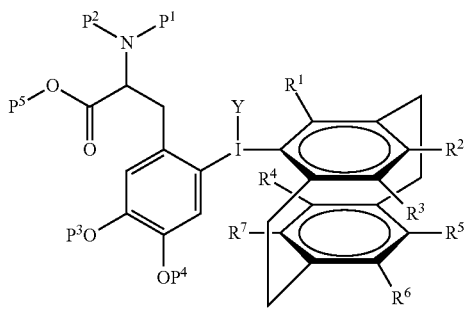

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group. For example, the compound of Formula (3) is:

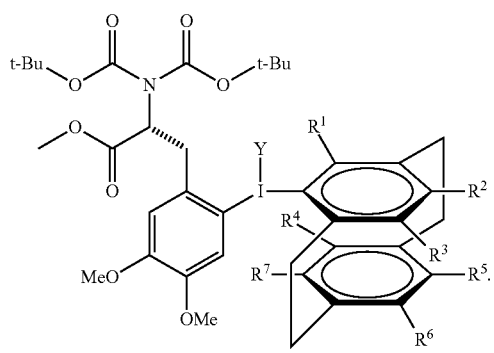

The methods described above can be useful in the preparation of fluorinated aryl and heteroaryl ring systems. In particular, the methods can be used to prepare radiolabeled fluorinated aryl and heteroaryl ring systems (e.g., PET radiotracers). Accordingly, provided herein is a method for making a compound of Formula (5):

Ar—F wherein Ar is a substituted or unsubstituted aryl or heteroaryl ring system as described herein. The method can include heating a solution comprising a compound MF, wherein M is a counter ion, and a compound of Formula (3). In some embodiments, F is $^{18}$F.

A compound according to Formula (2) or (5) can be chosen from:

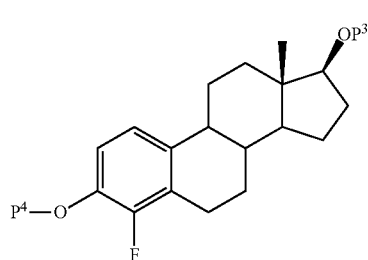

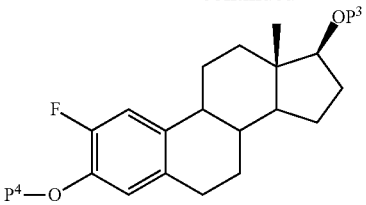

wherein each of $P^3$ and $P^4$ are independently an alcohol protecting group.

In some embodiments, a compound of Formula (2) or (5) is:

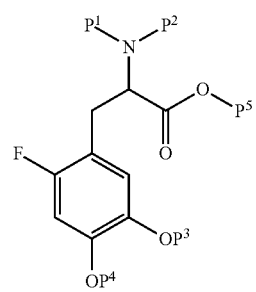

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group. For example, the compound of Formula (2) or (5) can be:

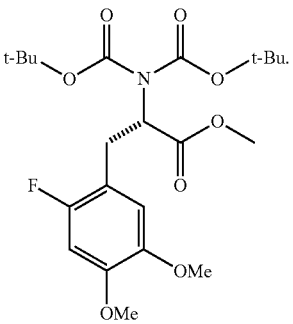

In some embodiments, a compound of Formula (2) or (5) is:

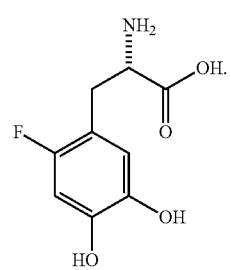 [SMILES: N[C@@H](Cc1cc(O)c(O)cc1F)C(=O)O]

For example, the compound can be chosen from:

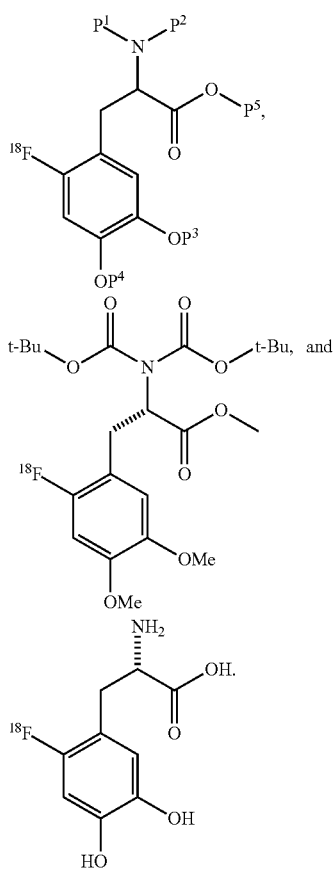

In some embodiments, a compound of Formula (2) or (5) can be

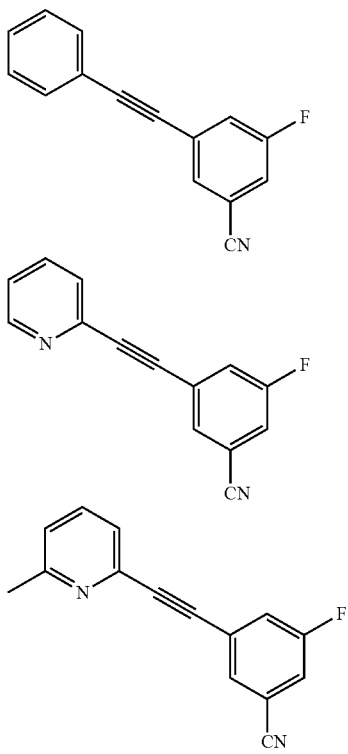

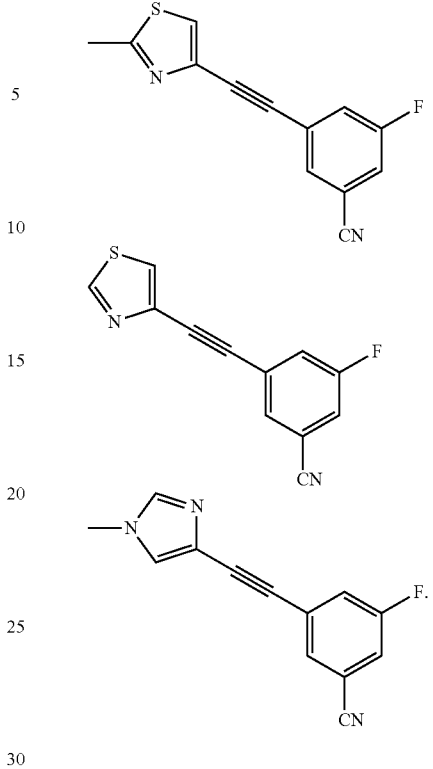

A nonpolar solvent can be any solvent having a dielectric constant of less than about 10. For example, a nonpolar solvent can be chosen from benzene, toluene, o-xylene, m-xylene, p-xylene, ethyl benzene, carbon tetrachloride, hexane, cyclohexane, fluorobenzene, chlorobenzene, nitrobenzene, and mixtures thereof. In some embodiments, the nonpolar solvent is selected from benzene, toluene, cyclohexane, and mixtures thereof In some embodiments the nonpolar solvent is a mixture, for example a mixture of cyclohexane and toluene.

A polar solvent is a solvent having a dielectric constant greater than about 10. In some embodiments, the polar solvent is a polar aprotic solvent, such as acetonitrile, acetone, dichloromethane, ethyl acetate, tetrahydrofuran, dimethylformamide, 1,2-difluorobenzene, benzotrifluoride, and mixtures thereof In some embodiments, the polar aprotic solvent is acetonitrile.

The methods described herein can further include filtering the solution to remove insoluble material prior to heating. In some embodiments, the insoluble material is a salt. In some cases, the solvent can be removed from the filtrate prior to heating. For example, the solvent can be removed and the filtrate can be dissolved in another solvent prior to heating. In some cases, the method can also include removing salt by chromatography (e.g., gel permeation chromatography). For example, if a polar solvent is used, it may be desirable to remove unwanted salts by chromatography prior to heating.

Heating can be accomplished by conventional means (e.g., heating bath, oven, heat gun, hot plate, Bunsen burner, heating mantle, and the like), by the use of a microwave, or by flash pyrolysis. Typically, the reaction mixture is heated at a temperature ranging from about 25° C. to about 250° C. (e.g., between about 80° C. to about 200° C., 100° C. to about 200° C., about 120° C. to about 170° C., about 120° C. to about 160° C., about 120° C. to about 150° C., and about 130° C. to about 150° C.). In some embodiments, the reaction mixture is heated to about 140° C.

Heating can occur for any time necessary to complete the reaction. For example, heating can occur for from about 1 second to about 25 minutes (e.g., from about 1 second to about 5 second; from about 1 second to about 10 seconds; from about 1 second to about 30 seconds; from about 1 second to about 1 minute; from about 1 second to about 2 minutes; from about 1 second to about 5 minutes; from about 1 second to about 8 minutes; from about 1 second to about 15 minutes; from about 1 second to about 20 minutes; from about 10 second to about 25 minutes; from about 30 seconds to about 25 minutes; from about 1 minute to about 25 minutes; from about 5 minutes to about 25 minutes; from about 10 minutes to about 25 minutes; from about 22 minutes to about 25 minutes; from about 5 to about 30 seconds; from about 30 seconds to about 2 minutes; from about 2 minutes to about 5 minutes; from about 5 minutes to about 10 minutes; from about 5 minutes to about 15 minutes; from about 3 minutes to about 8 minutes; from about 8 minutes to about 16 minutes; and from about 12 minutes to about 20 minutes). In some embodiments, heating can occur for from about 1 second to about 15 minutes.

In the methods described herein, a pressure tube or other reinforced closed system can be used in instances where the desired temperature is above the boiling point of the solvent utilized.

The reaction can be conducted in the presence of an inert gas such as nitrogen or argon. In some embodiments, steps are taken to remove oxygen and/or water from the reaction solvent and starting materials. This can be accomplished by a number of methods including distillation of solvents in the presence of agents that react with and/or sequester water and under an atmosphere of inert gas, and purging the reaction vessel with an inert gas.

The methods described herein can be used when MX (e.g., MF) is reacted in an amount ranging from about 1 picomole to about 10 millimoles (e.g., about 1 picomole to about 5 millimoles; about 1 picomole to about 1 millimole; about 1 picomole to about 500 micromoles; about 1 picomole to about 100 micromoles; about 1 picomole to about 50 micromoles; about 1 picomole to about 5 micromoles; about 1 picomole to about 1 micromole; about 1 picomole to about 500 nanomoles; about 1 picomole to about 100 nanomoles; about 1 picomole to about 50 nanomoles; about 1 picomole to about 5 nanomoles; about 1 picomole to about 1 nanomole; about 100 picomoles to about 10 millimoles; about 500 picomoles to about 10 millimoles; about 1 nanomole to about 10 millimoles; about 50 nanomoles to about 10 millimoles; about 100 nanomoles to about 10 millimoles; about 500 nanomoles to about 10 millimoles; about 1 micromole to about 10 millimoles; about 50 micromoles to about 10 millimoles; about 100 micromoles to about 10 millimoles; about 500 micromoles to about 10 millimoles and about 1 millimole to about 10 millimoles). In some embodiments, MX is reacted in the sample in an amount of less than about 10 millimoles. In many cases, the compound of Formula (3) is used in an excess when compared to the amount of MX present in the sample. In some embodiments, the reaction mixture having MX further contains additional compounds which may be present in an excess compared to MX. For example, the additional compounds may be present in more than one million fold excess compared to MX.

EXAMPLES

General Methods
  Synthesis.
  All materials were obtained from commercial sources and used as received unless otherwise noted. Zinc chloride melted under dynamic vacuum before use. Diethyl ether was distilled under reduced pressure from sodium/benzophenone. Tetrabutylammonium azide (TBAN$_3$), tetrabutylammonium thiocyanate (TBASCN), sodium phenoxide (NaOPh), sodium thiophenoxide (NaSPh), and sodium trifluoroethoxide (NaOCH$_2$CF$_3$) were dried at room temperature in a drying pistol (charged with P$_2$O$_5$) under dynamic vacuum for one week. Acetonitrile and d$_3$-acetonitrile were heated at reflux over P$_2$O$_5$, distilled into flame-dried storage tubes, and transferred to an inert atmosphere glove box. Benzene and d$_6$-benzene were heated at reflux over CaH$_2$ overnight and distilled directly into flame-dried storage tubes under dry nitrogen. Tetrahydrofuran (THF) was dried over Na/benzophenone and distilled into a flame dried storage flask under dry nitrogen. All glassware, syringes, and NMR tubes were oven dried (140° C.) for more than 24 h before they were transferred into the glove box for use. All NMR experiments reported here were performed using Bruker spectrometers (400, 500, and 600 MHz) at the University of Nebraska-Lincoln. Yields from NMR scale reactions were determined by using the residual solvent peak as an internal standard. Additional product analyses were performed by GC-MS.

General Procedure for Reductive Elimination Reactions.

In a N$_2$ charged glove box, 0.025 mmol of an iodonium salt was dissolved in 0.3 mL of dry d$_3$-acetonitrile. The solution was combined with 0.3 mL d$_3$-acetonitrile solution of 1 equiv. of the appropriate salt (TBAN$_3$ (7.1 mg), TBASPh (8.8 mg), NaOPh (2.9 mg) NaOCH$_2$CF$_3$ (3.1 mg)). The mixture was transferred into a J-Young NMR tube, sealed, taken out of the glove box and an initial NMR spectrum was taken. The NMR tube was wrapped with aluminum foil and put into a 45° C. oil bath. (For acetate and thiocyanate, more vigorous conditions were required. The solutions containing TBAOAc (15 mg) and TBASCN (7.5 mg) were heated in an 80° C. oil bath.) The progress of the reaction was monitored by $^1$H NMR until no I(III) species was left. Product analysis was performed by $^1$H NMR and GC-MS.

Calculations.

All calculations were performed using the Gaussian suite of programs and visualization was performed with GaussView. Ground state geometries were identified after driving the C-C-I-H dihedral angle through a full range of motion. Structures were optimized and their energies calculated using DFT B3LYP/DGDZVP methods. Frequency calculations on minimized structures were performed to make the zero point energy and thermal corrections. Transition states were optimized at the same computational level.

Example 1

Computational study of [2,2]paracyclophan-4-yl iodonium salts

Azide transfer in diaryliodonium salts was investigated through a computational study as described above. Ground and transition state energies were calculated for a highly simplified model of azide substitution, loss of HI from the HIN3Ar complexes of p-xylene and [2.2]paracyclophane. For this study, diaryliodonium azides were used as they are known to undergo reductive elimination at or near room temperature (see J. J. Lubinkowski et al., *J. Org. Chem.* 1978, 43, 2432; and V. V. Grushin et al., *Izv. Akad. Nauk SSSR, Ser. Khim.* 1984, 2332), and because the small azide nucleophile has a relatively modest steric demand. The results of the computational study are show in FIG. 1.

Inspection of FIG. 1 shows that movement from the ground state to the transition state geometries for azide substitution is accompanied by ipso carbon rehybridization and deflection of the HI group out of the plane. For the xylyl derivative the C4-C1-I angle is 161.9°. However, in the [2.2]paracyclophan-4-yl transition state structure the significant steric demand of the second ring in the planar chiral ligand inhibits out of plane movement of the iodine atom (C4-C1-I angle is)167.2°. This structural difference is associated with an energetic penalty; the calculated free energy of activation for reductive elimination of HI from the p-xylene salt is 13.7 kcal/mol, while the barrier for the cyclophane derivative is 4.8 kcal/mol higher. These results indicate that an increase in steric demand above the plane of the aromatic ring destabilizes the reductive elimination transition state. For the [2.2]paracyclophan-4-yl iodonium salt, this effect is sufficiently large to provide stereoelectronic control of unidirectional reductive elimination (SECURE).

Example 2

Preparation of ([2.2]paracyclophan-4-yl)(2',5'-dimethylphenyl)iodonium hexafluorophosphate (1)

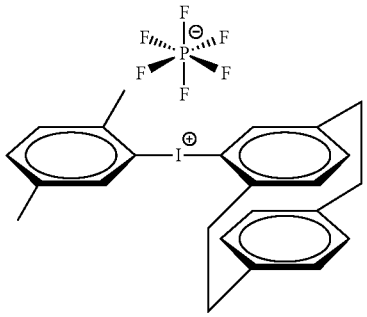

In a 50 mL Schlenk tube under nitrogen, a stirred solution of 4-bromocyclophane (1 mmol, 282 mg) in 10 mL of anhydrous diethyl ether was cooled to −78° C. A solution of t-BuLi (1.7 M in pentane, 2.3 equiv.) was added dropwise and the resulting mixture was stirred at −78° C. for 20 minutes and then warmed to 0° C. and allowed to stir for an additional 20 min. The reaction mixture was cooled again to −78° C. before a solution of zinc chloride (200 mg, 1.5 mmol) in ether (10 mL) was added dropwise by cannula. After the addition, the reaction mixture was allowed to warm to room temperature over the course of one hour before the solvents were removed in vacuo. The remaining solid was dissolved in anhydrous $CH_3CN$ and the solution was cooled to −40° C. and added dropwise to precooled (−40° C.) suspension of bis(acetyloxy)-(2,5-dimethylphenyl)-$\lambda_3$-iodane (350 mg, 1 mmol) in 10 mL of acetonitrile. The mixture was allowed to warm to room temperature over 30 minutes before the solvent was removed in vacuo. The resulting solid was washed with hexanes and then dissolved in aqueous acetonitrile. Addition of an aqueous $NaPF_6$ solution precipitated the product, which was extracted from the aqueous mixture with $CH_2Cl_2$. The organic layer was evaporated, dissolved in a minimal amount of $CH_2Cl_2$, precipitated with hexanes, filtered and dried in vacuo to yield 1 (105 mg, 18% yield).

Example 3

Preparation of (2,5-dimethylphenyl)(4'-methoxyphenyl)iodonium hexafluorophosphate (2)

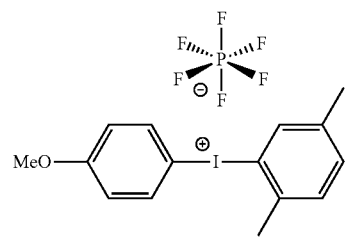

In a $N_2$ charged glove box, 1-(diacetoxyiodo)-4-methoxybenzene (352 mg, 1 mmol) was dissolved in 1.5 mL of dry acetonitrile. The solution was combined with a solution of p-toluenesulfonic acid monohydrate (190 mg, 1 mmol) in 1.5 mL of dry acetonitrile. p-Xylene (117 mg, 1.1 mmol) was added and the mixture was allowed to stand at room temperature for 2 h. Water (10 mL) was added and the mixture was extracted (3×5 mL) with hexanes. The water layer was treated with $NaPF_6$ (502 mg, 3 mmol) and the white precipitate was extracted from the aqueous layer with $CH_2Cl_2$. Evaporation of the organic solvent followed by recrystallization from diethyl ether/dichloromethane gave 309 mg (65.2%) of (2,5-dimethylphenyl)-(4'-methoxyphenyl)iodonium hexafluorophosphate.

Example 4

Preparation of ([2.2]paracyclophan-4-yl)(4'-methoxyphenyl)iodonium hexafluorophosphate (3)

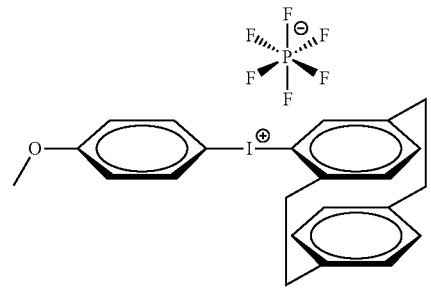

In a 50 mL Schlenk tube under nitrogen, a stirred solution of bromocyclophane (1 mmol, 282 mg) in 10 mL of anhydrous diethyl ether was cooled to −78° C. A solution of t-BuLi (1.7 M in pentane, 2.3 equiv.) was added dropwise and the resulting mixture was stirred at −78° C. for 20 minutes and then warmed to 0° C. and allowed to stir for an additional 20 min. The reaction mixture was cooled again to −78° C. before a solution of zinc chloride (200 mg, 1.5 mmol) in ether (10 mL) was added dropwise by cannula. After the addition, the reaction mixture was allowed to warm to room temperature over the course of one hour before the solvents were removed in vacuo. The remaining solid was dissolved in anhydrous $CH_3CN$ and the solution was cooled to −40° C. and added dropwise to precooled (−40° C.) suspension of bis(acetyloxy)-(4-methoxyphenyl)-$\lambda_3$-iodane (352 mg, 1 mmol) in 10 mL of acetonitrile. The mixture was allowed to warm to room temperature over 30 minutes before the solvent was removed in vacuo. The resulting solid was washed with hexanes and then dissolved in aqueous acetonitrile. Addition of an aqueous NaPF$_6$ solution precipitated the product, which was extracted from the aqueous mixture with CH$_2$Cl$_2$. The organic layer was evaporated, dissolved in a minimal amount of CH$_2$Cl$_2$, precipitated with hexanes, filtered and dried in vacuo (225 mg, 38.4% yield).

Example 5

Preparation of (7-methoxy[2.2]paracyclophanyl)(4'-methoxyphenyl)iodonium hexafluorophosphate (4)

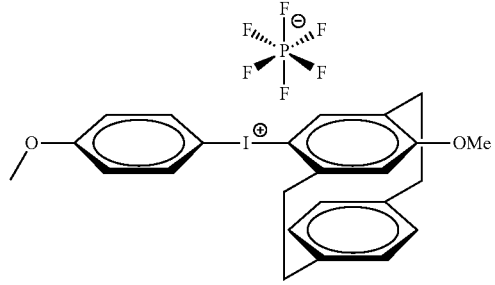

In a 100 mL Schlenk tube, 4-methoxy-7-bromo[2.2]paracyclophane (1.26 mmol, 400.6 mg) was dissolved in 25 mL of distilled ether and cooled to −78° C. To the cooled solution, 1.7M t-butyl lithium (3.16 mmol, 1.85 mL) was added dropwise and the stirred solution was held at −78° C. for 1 hour. A solution of anhydrous zinc chloride (1.51 mmol, 206.1 mg) in 10 mL of diethyl ether was added dropwise to the cooled solution. The mixture was allowed to warm to room temperature, and the solvent was removed under reduced pressure. The residual solid (organozinc chloride reagent and lithium salts) was taken up in anhydrous acetonitrile and cooled to −40° C. before a solution of 4-methoxy(diacetoxyiodo)benzene (1.89 mmol, 665.5 mg) in acetonitrile (10 mL) was added in a dropwise fashion. After 1 hour at −40° C., the mixture was warmed to room temperature and the solvent was removed under reduced pressure. Deionized water and sodium hexafluorophosphate (410 mg) were added, followed by 50 mL of dichloromethane. The mixture was transferred to a separatory funnel and the organic phase was separated. The solvent was removed by rotary evaporation and the remaining solid was dissolved in 5 mL of dichloromethane and dripped into 150 mL hexanes. The precipitate was aged for one hour, collected by gravity filtration, and dried in vacuo to yield a colorless salt (55.6%, 431.7 mg).

Example 6

Reductive Elimination from Iodonium Salts

To compare the directing effects of the electronically similar p-xylyl and [2.2]paracylcophan-4-yl groups, a series of unsymmetrical iodonium salts were prepared by the methods described in Examples 2-4 (see Table 1) and arene functionalization by various nucleophiles (X) was investigated (see Scheme 3). The salts underwent reductive elimination using the general methods described above.

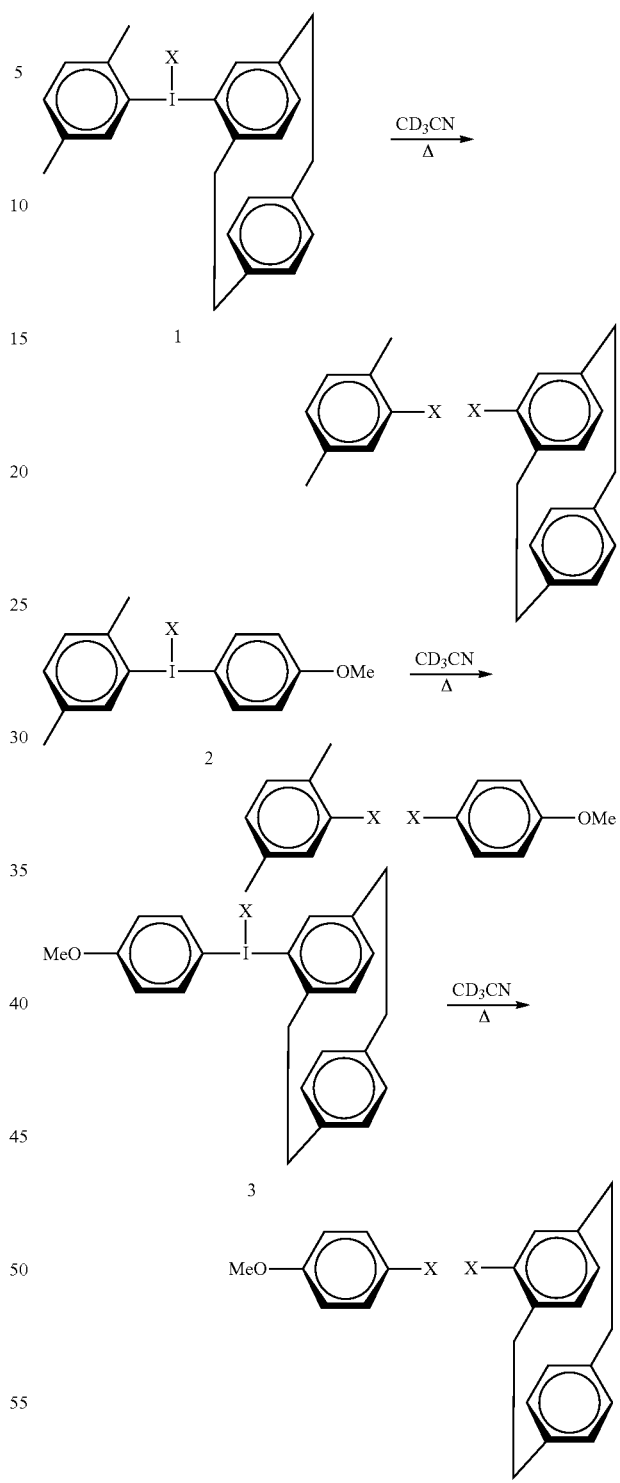

Scheme 3.

When compound 1 was treated with TBAN$_3$ and heated at 45° C. in CD$_3$CN (0.04 M), conversion of the diaryliodonium azide was complete within a few hours. The azidoxylene was formed exclusively in excellent yield, and no azidocyclophane was observed at the detection limit of $^1$H NMR spectroscopy. This unidirectional elimination was also observed with thiocyanate, phenoxide, thiophenoxide, trifluoroethoxide, and acetate (Table 1). The observed selectivity (>99:1) corresponds to a difference in the free energies of activation (DDG$^‡$) of at least 2.8 kcal/mol.

To provide context for the results obtained for compound 1, arene functionalization by various nucleophiles (X) in compound 2 was investigated. The regioselectivity observed during the reductive elimination of cyclophanyl-substituted diaryliodonium salts mirrors that of 4-methoxyphenyl derivatives (Table 1). The 4-methoxyphenyl moiety is one of the most effective, commonly employed directing group in diaryliodonium chemistry, perfect regioselectivity for arene functionalization, however, is not observed with this directing group. For the redox active thiophenoxide and phenoxide nucleophiles, some loss of regiocontrol was evident and functionalized anisoles were formed.

To test the relative directing group abilities of 4-methoxyphenyl and [2.2]paracyclophan-4-yl substituents, the unsymmetrical I(III) derivative of compound 3 were prepared from 4-methoxy(diacetoxyiodo)benzene (38% yield) and its thermal decomposition chemistry examined. More vigorous reaction conditions (80° C., $CD_3CN$) were necessary to promote speedy carbon-heteroatom bond formation with acetate and thiocyanate from 3 in comparison to 1 or 2. As can be seen from inspection of Table 1, the directing group ability of the [2.2]paracyclophane ligand is comparable or slightly superior to that of the 4-methoxyphenyl substituent on I(III).

TABLE 1

Yields of reductive elimination products from I(III) salts

| X | 1 | | 2 | | 3 | |
|---|---|---|---|---|---|---|
| $N_3$ | 99< | 0 | 99< | 0 | 86 | 14 |
| OAc | 85 | 0 | 99< | 0 | 68 | 31 |
| OPh | 87 | 0 | 96 | 4 | 51 | 40 |
| $OCH_2CF_3$ | 82 | 0 | 80 | 0 | 19 | 39 |
| SCN | 99< | 0 | 99< | 0 | 81 | 18 |
| SPh | 98 | 0 | 95 | 5 | 43 | 52 |

As shown in Table 1, it appears that for oxygen or sulphur nucleophiles the directing group ability of the cyclophane ligand diminishes as nucleophile basicity and the driving force for functionalizing the more electron-poor ring increase. Such a trend is consistent with Hammond's postulate and a concerted, reductive elimination mechanism in which less steric strain is developed at the cyclophane ipso carbon atom as the reaction becomes more exergonic.

Example 7

Kinetics of Reductive Elimination

The kinetics of aryl azide formation from $N_3$ salts of 1, 2 and 3 were investigated to probe the relative steric and electronic contributions to the observed regioselectivity. The salts underwent reductive elimination using the general method described above. The observed rate constants for xylyl azide formation ($CD_3CN$, 45° C.) were $4.2 \times 10^{-4}$ $s^{-1}$, $5.5 \times 10^{-5}$ $s^{-1}$, and $3.3 \times 10^{-6}$ $s^{-1}$, corresponding to free energies of activation of 21.7, 22.9, and 24.6 kcal/mol for the reactions of 1, 2 and 3, respectively. The fact that the rate constant for formation of azidoxylene is greater for 1 than 2 indicates that 4-iodo-[2.2]paracyclophane is a better leaving group than 4-iodoanisole. Since leaving group ability is correlated with the electron density on iodine in the aryl iodide being reductively eliminated, these kinetic data show experimentally that the [2.2]paracyclophane ligand is a more electron-poor aryl substituent than 4-methoxyphenyl and that steric destabilization of the transition state is responsible for the enhanced directing group ability of the [2.2]paracyclophane ligand.

Example 8

Reductive Elimination with Regiochemical Control

The reductive elimination of compound 4 with various nucleophiles (X) was studied. The salts underwent reductive elimination using the general method described above. This compound features an electron donating methoxy substituent para to the I(III) center.

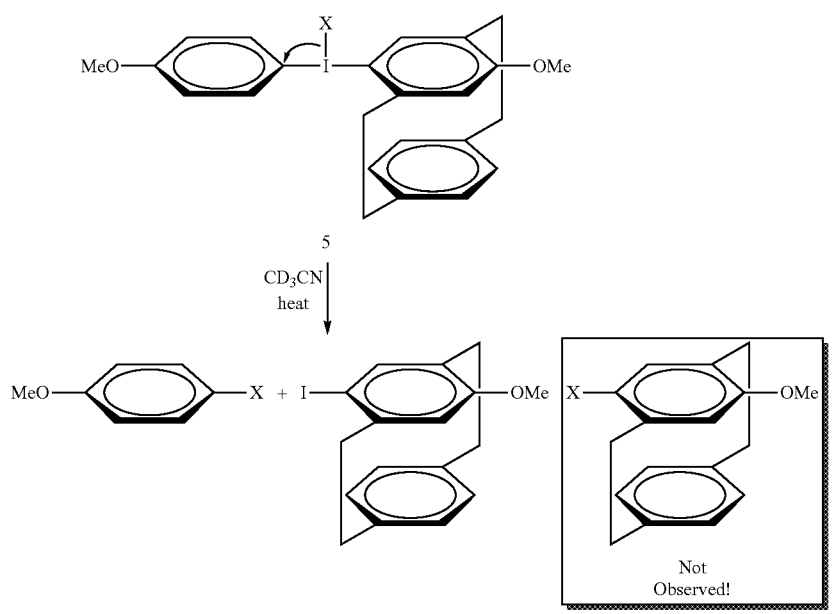

Scheme 4.

X = $N_3$  96%
X = OAc  51%
X = OPh  84%
X = SCN  92%
X = SPh  82%

As shown in Scheme 4, only anisole substitution was observed after the thermal decomposition of the azide, acetate, phenoxide, thiocyanate, and thiophenoxide salts. However, a mixture of cyclophane- (30%) and anisole-substituted (60%) products was obtained from the reductive elimination of the 2,2,2-trifluoroethoxide salt of 4. The reason for the breakdown in regioselectivity was clear from the product analysis, which shows roughly equal amounts of 3- and 4-(2,2,2-trifluoroethoxy)anisole, as well as roughly equal amounts of the two $CF_3CH_2O$-substituted cyclophane regioisomers. This lack of selectivity and distribution of regioisomers is consistent with a change in mechanism to one involving benzyne intermediates. For this basic nucleophile, the strategy of raising the transition state energy for reductive elimination of the aryl iodide enables the benzyne reaction manifold to be competitive.

Example 9

Fluorination of (4-methoxyphenyl)-(5-methoxy-4-[2.2]paracyclophanyl)-iodonium hexafluorophosphate In a $N_2$ charged glove box, 12.3 mg of (4-methoxyphenyl)-4-[2.2]paracyclophanyliodonium hexafluorophosphate (0.02 mmol) was dissolved in 0.3 mL of dry acetonitrile, to which a solution of 1 mg anhydrous TMAF (1 equivalent) in 0.3 mL of dry acetonitrile was added dropwise. The solvent was evaporated, and the remainder was dissolved in 0.6 mL of $d_6$-benzene, passed through a 0.2 mm PTFE syringe filter, and transferred into a J-Young NMR tube. The tube was sealed, taken out of the box, and heated in a 140° C. oil bath for 15 minutes. Yields of fluorinated arenes were determined by $^1H$ and $^{19}F$ NMR spectroscopy and confirmed by GC-MS. 4-fluoroanisole was formed in 52% yield, 3-fluoroanisole in 24% yield, the rest of the fluoride ended up as unidentified inorganic species (singlet at −128.1 ppm and multiplets at −130.7 ppm in $^{19}F$ NMR).

For this salt, decomposition was also performed at 80° C., the reaction took 5 hours to finish and 4-fluoroanisole was formed in 66% yield, 3-fluoroanisole in 15% yield.

A number of embodiments of the invention have been described. Nevertheless, it will be understood that various modifications may be made without departing from the spirit and scope of the invention. Accordingly, other embodiments are within the scope of the following claims.

What is claimed is:
1. A compound of Formula (1):

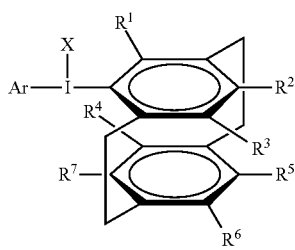

wherein:
Ar is a substituted or unsubstituted aryl or heteroaryl ring system;
X is either a moiety wherein the pKa of the acid H—X is less than 12 or a leaving group;
$R^1$ is hydrogen or a substituent having a Hammett $\sigma_p$ value of less than zero; and
$R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, —$SR^8$, —$SOR^8$, halo, $SO_2R^8$, $(CH_2)_nOR^8$, C(=O)$NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;
each m and n is independently an integer from 0 to 10; and
each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

2. The compound of claim 1, wherein X comprises a radioactive isotope.

3. The compound of claim 1, wherein X is selected from the group consisting of halide, aryl carboxylate, alkyl carboxylate, phosphate, phosphonate, phosphonite, azide, thiocyanate, cyanate, phenoxide, triflate, trifluoroethoxide, thiolates, and stabilized enolates.

4. The compound of claim 1, wherein X is selected from the group consisting of: fluoride, chloride, bromide, iodide, triflate, trifluoroacetate, benzoate, acetate, phenoxide, trifluoroethoxide, cyanate, azide, thiocyanate, thiolates, phosphates, and stabilized enolates.

5. The compound of claim 4, wherein X is fluoride.

6. The compound of claim 5, wherein X is $^{18}F$.

7. The compound of claim 1, wherein X is selected from the group consisting of: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, chloride, bromide, and iodide.

8. The compound of claim 1, wherein $R^1$ is selected from the group consisting of: —$(C_1-C_{10})$alkyl, —$(C_1-C_{10})$haloalkyl, $(C_2-C_{10})$alkenyl, $(C_2-C_{10})$alkynyl, —O—$(C_1-C_{10})$alkyl, —C(O)—O—$(C_1-C_{10})$alkyl, aryl, and heteroaryl.

9. The compound of claim 8, wherein $R^1$ is —O-$(C_1-C_{10})$alkyl.

10. The compound of claim 9, wherein $R^1$ is $OCH_3$.

11. The compound of claim 1, wherein Ar is an electron rich aryl or heteroaryl ring system.

12. The compound of claim 11, wherein Ar—H is more easily oxidized than benzene.

13. The compound of claim 1, wherein Ar is chosen from a phenylalanine derivative, tyrosine derivative, tryptophan derivative, histidine derivative, and estradiol derivative.

14. The compound of claim 1, wherein the compound of Formula (1) is a compound of Formula (1A):

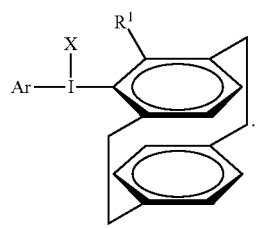

15. The compound of claim 1, wherein Ar is selected from the group consisting of:

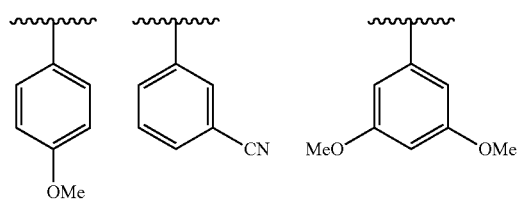
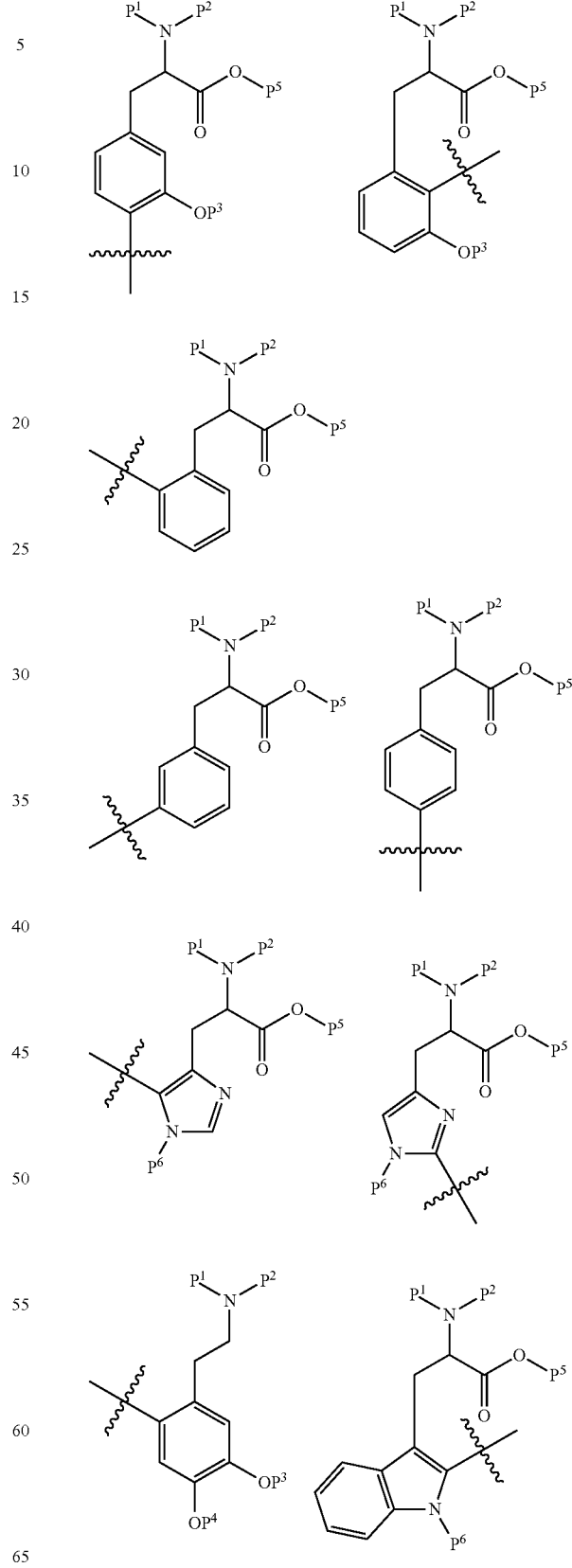

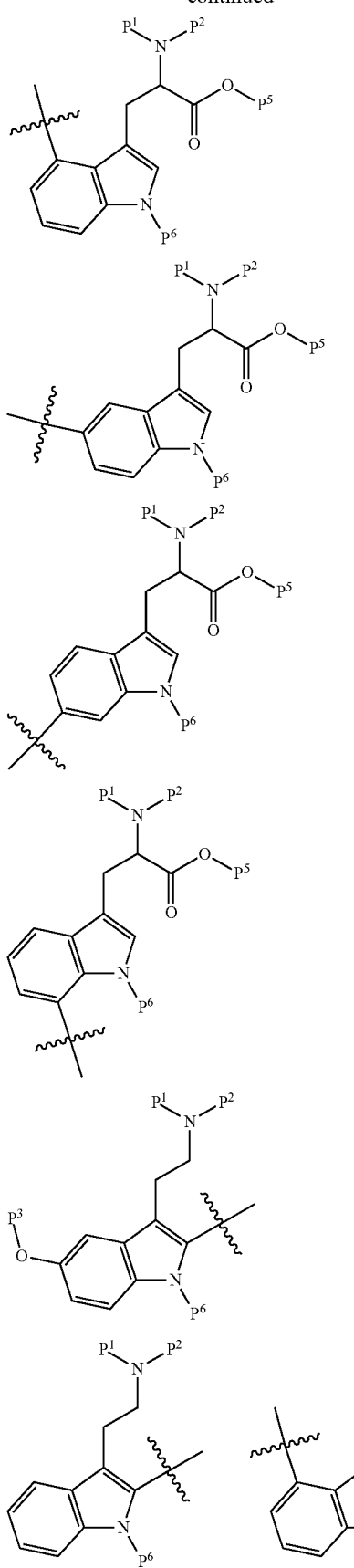
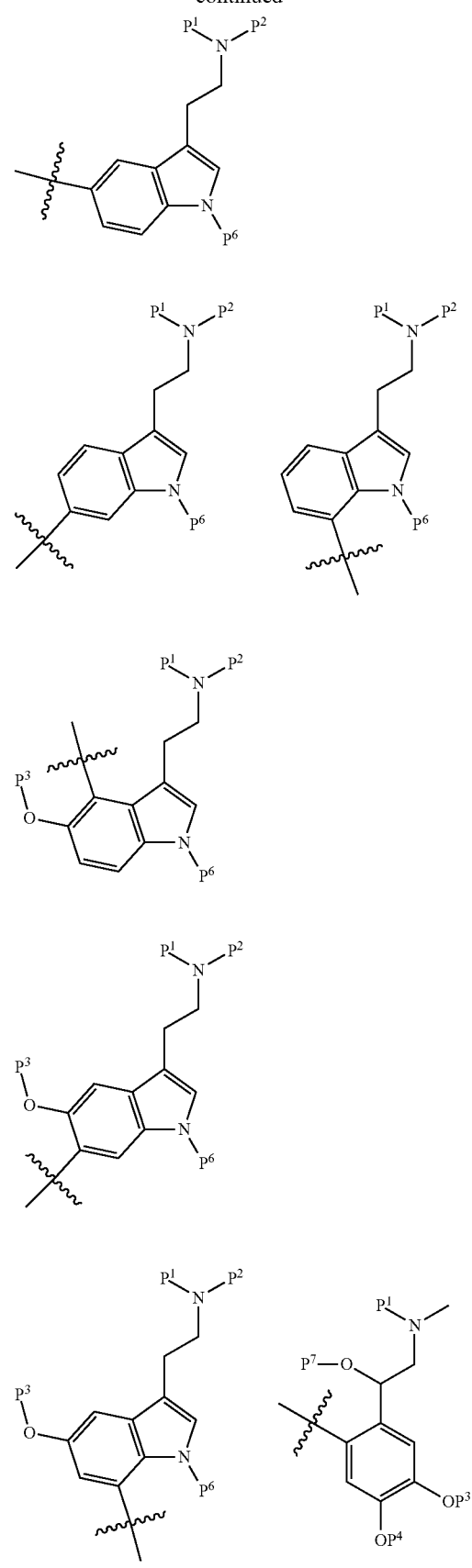

-continued

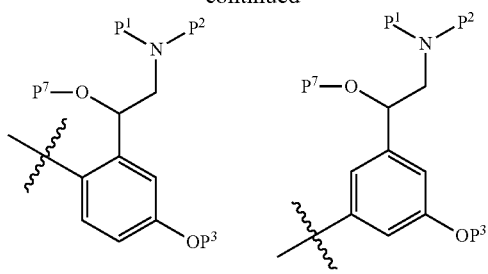

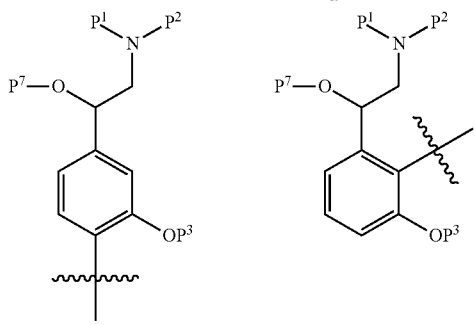

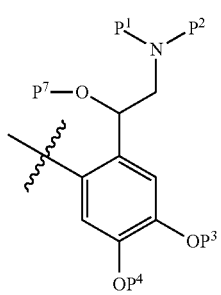

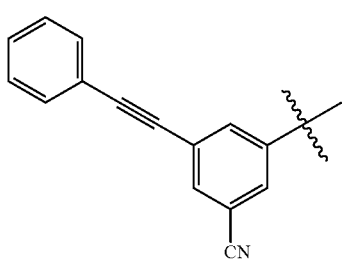

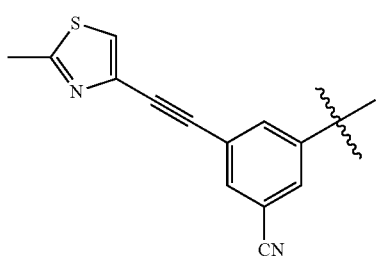

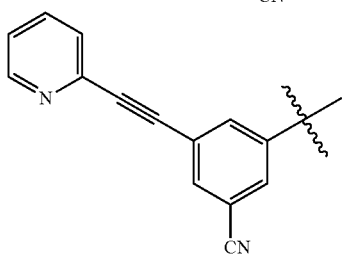

-continued

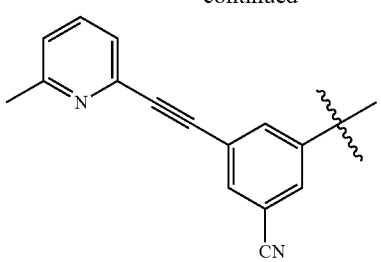

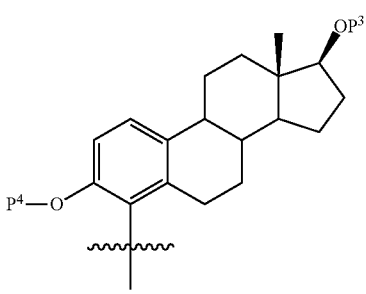

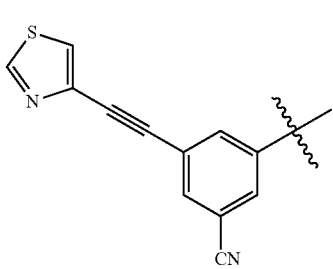

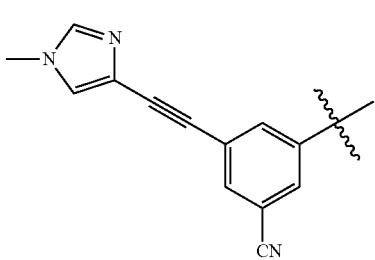

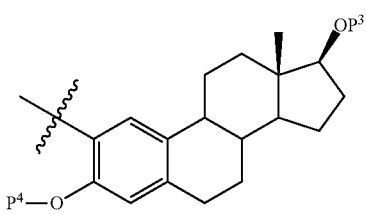

wherein:
each of $P^1$, $P^2$ and $P^6$ are independently a nitrogen protecting group, or $P^1$ and $P^2$ come together to form a single nitrogen protecting group;
each of $P^3$, $P^4$, and $P^7$ are independently an alcohol protecting group, or $P^3$ and $P^4$ come together to form a single oxygen protecting group; and
$P^5$ is a carboxylic acid protecting group.

16. The compound of claim 1, wherein the compound of Formula (1) is selected from the group consisting of:

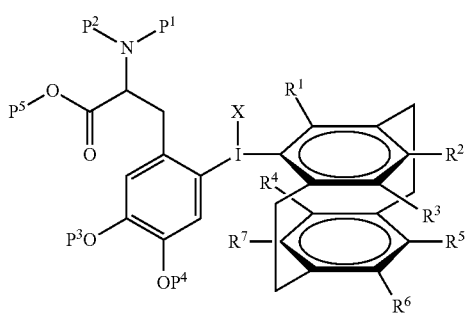

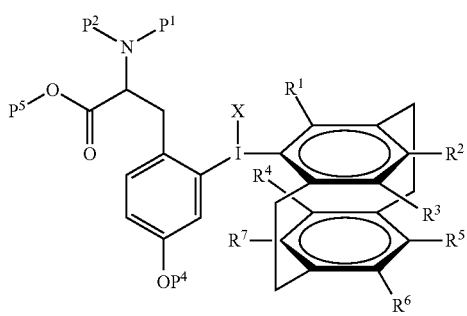

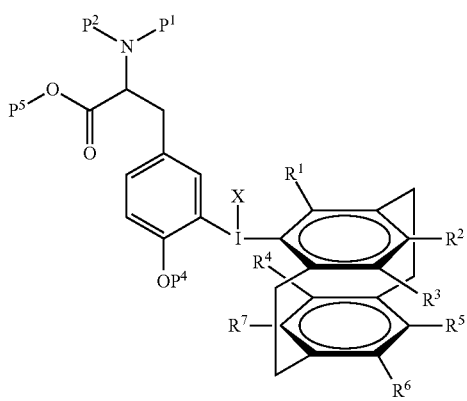

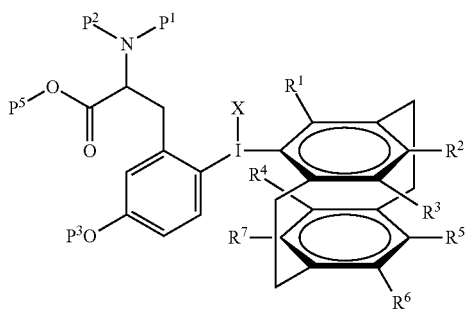

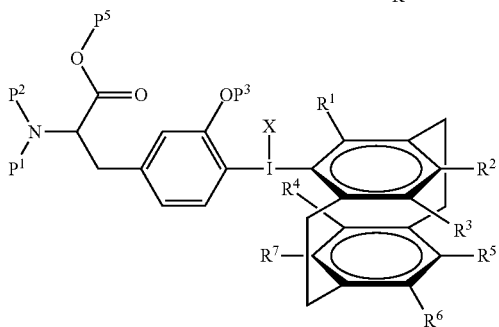

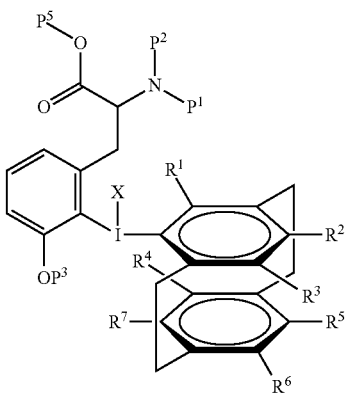

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

17. The compound of claim 1, wherein the compound of Formula (1) is selected from the group consisting of:

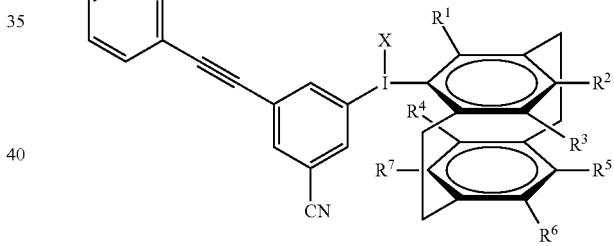

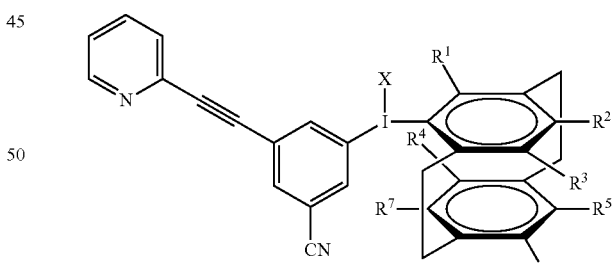

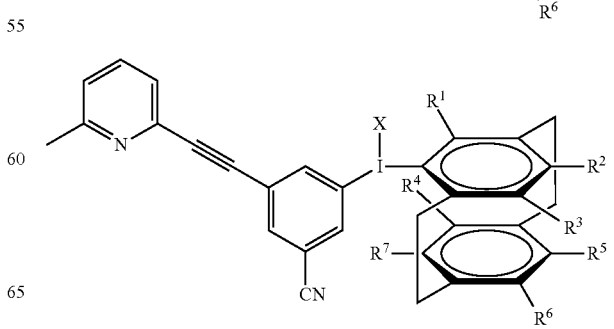

61
-continued

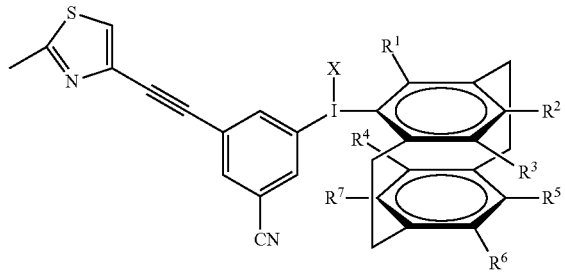

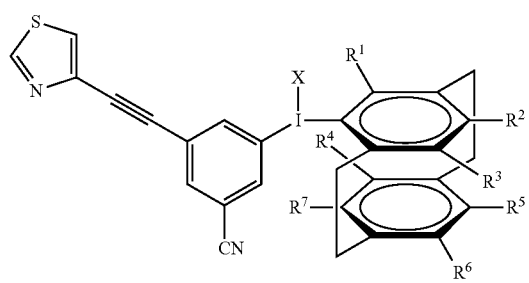

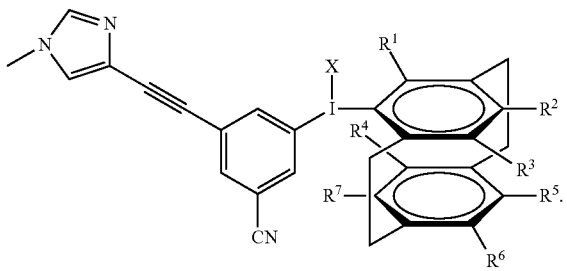

18. The compound of claim 1, wherein the compound of Formula (1) is selected from the group consisting of:

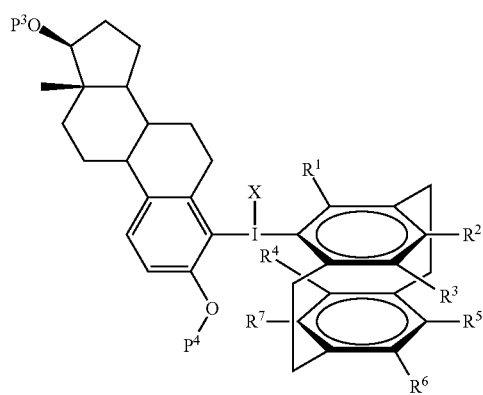

62
-continued

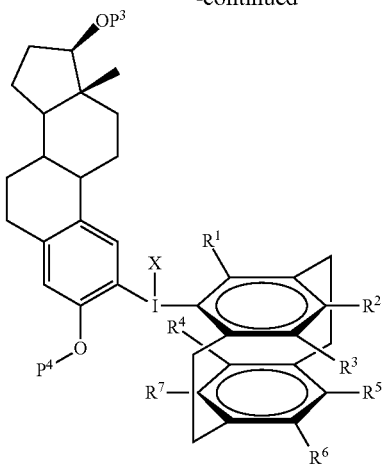

wherein:
each of $P^3$ and $P^4$ are independently an alcohol protecting group.

19. The compound of claim 1, wherein the Ar moiety is enantiomerically enriched.

20. The compound of claim 19, wherein the Ar moiety is present in an enantiomeric excess of at least 75%.

21. The compound of claim 19, wherein the Ar moiety is present in an enantiomeric excess of at least 95%.

22. The compound of claim 19, wherein the Ar moiety is present in an enantiomeric excess of at least 98%.

23. A method of making a compound of Formula (2):

$$Ar-X$$

wherein:
Ar is a substituted or unsubstituted aryl or heteroaryl ring system; and
X is a moiety wherein the pKa of the acid H—X is less than 12;
the method comprising heating a solution comprising a compound MX, wherein M is a counter ion, and a compound of Formula (3):

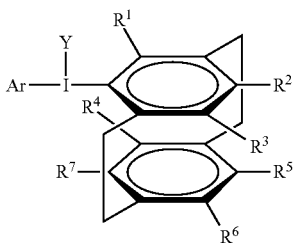

wherein:
Ar is a substituted or unsubstituted aryl or heteroaryl ring system;
Y is a leaving group;
$R^1$ is hydrogen or a substituent having a Hammett $\sigma_p$ value of less than zero; and
$R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, —$SR^8$, —$SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

each m and n is independently an integer from 0 to 10; and each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

24. The method of claim 23, wherein M is selected from the group consisting of: potassium; sodium; cesium; complexes of lithium, sodium, potassium, or cesium with cryptands or crown ethers; tetrasubstituted ammonium cations; and phosphonium cations.

25. The method of claim 23, wherein the solution further comprises a non-polar solvent.

26. The method of claim 25, wherein the nonpolar solvent is selected from the group consisting of: benzene, toluene, o-xylene, m-xylene, p-xylene, ethyl benzene, carbon tetrachloride, hexane, cyclohexane, fluorobenzene, chlorobenzene, nitrobenzene, and mixtures thereof.

27. The method of claim 25, wherein the method further comprises filtering the solution to remove insoluble material prior to heating.

28. The method of claim 27, wherein the solvent is removed from the filtrate prior to heating.

29. The method of claim 23, wherein the solution further comprises a polar solvent.

30. The method of claim 29, wherein the polar solvent is chosen from: acetonitrile, acetone, dichloromethane, ethyl acetate, tetrahydrofuran, dimethylformamide, 1,2-difluorobenzene, benzotrifluoride and mixtures thereof.

31. The method of claim 29, wherein the method further comprises filtering the solution to remove insoluble material prior to heating.

32. The method of claim 31, wherein the solvent is removed from the filtrate prior to heating.

33. The method of claim 29, wherein the method further comprises removing salt by chromatography.

34. The method of claim 33, wherein the chromatography is gel permeation chromatography.

35. The method of claim 23, wherein the heating comprises heating at a temperature ranging from about 25° C. to about 250° C.

36. The method of claim 23, wherein the heating occurs for from about 1 second to about 25 minutes.

37. The method of claim 36, wherein the heating is accomplished by a flash pyrolysis method, a conventional heating method, or by a microwave method.

38. The method of claim 23, wherein the compound of Formula (2) is chosen from:

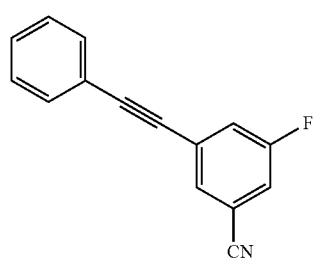

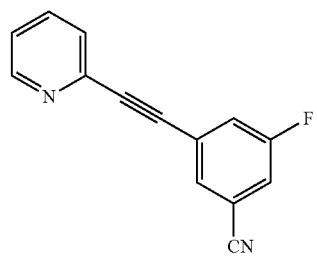

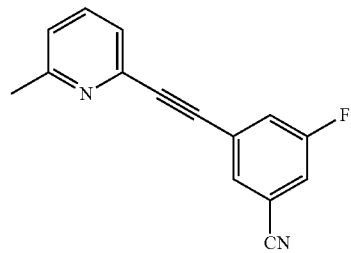

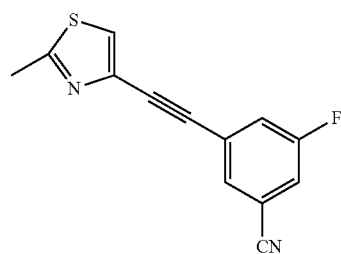

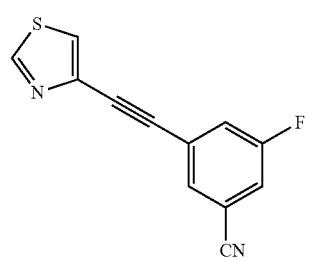

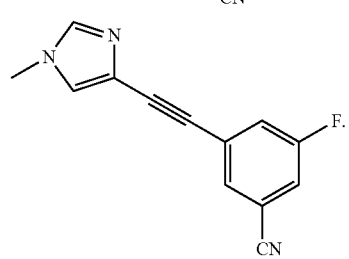

39. The method of claim 23, wherein the compound of Formula (2) is chosen from:

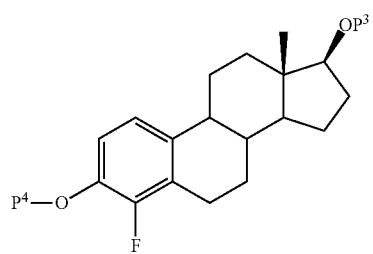

-continued

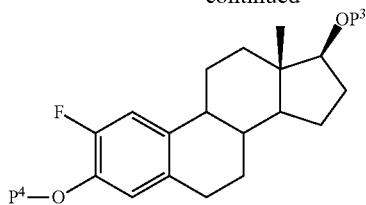

wherein:
each of P³ and P⁴ are independently an alcohol protecting group.

40. The method of claim 23, wherein the compound of Formula (2) is:

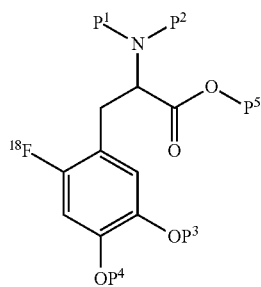

wherein:
each of P¹ and P² are independently a nitrogen protecting group, or P¹ and P² come together to form a single nitrogen protecting group;
each of P³, and P⁴ are independently an alcohol protecting group, or P³ and P⁴ come together to form a single oxygen protecting group; and
P⁵ is a carboxylic acid protecting group.

41. The method of claim 40, wherein the compound of Formula (2) is:

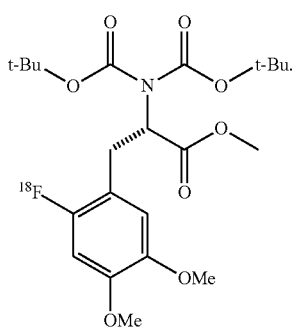

42. The method of claim 23, wherein the compound of Formula (2) is:

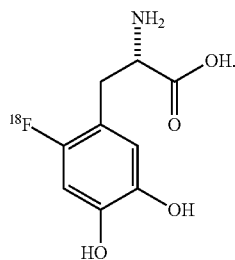 [SMILES: N[C@@H](Cc1cc(O)c(O)cc1[18F])C(=O)O]

43. A compound of Formula (4):

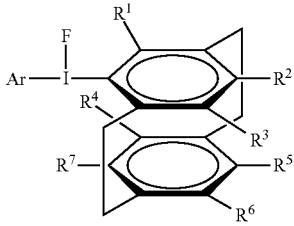

wherein:
Ar is a substituted or unsubstituted aryl or heteroaryl ring system;
$R^1$ is hydrogen or a substituent having a Hammett $\sigma_p$ value of less than zero; and
$R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, —$SR^8$, —$SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;
each m and n is independently an integer from 0 to 10; and
each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

44. A method of making a compound of Formula (5):

Ar—F wherein:
Ar is a substituted or unsubstituted aryl or heteroaryl ring system;
the method comprising heating a solution comprising a compound MF, wherein M is a counter ion, and a compound of Formula (3):

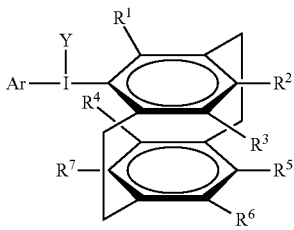

wherein:
Ar is a substituted or unsubstituted aryl or heteroaryl ring system;
Y is a leaving group;
$R^1$ is hydrogen or a substituent having a Hammett $\sigma_p$ value of less than zero; and
$R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, —$SR^8$, —$SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

each m and n is independently an integer from 0 to 10; and each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

45. The compound of claim 43, wherein F is $^{18}F$.

46. The compound of claim 43, wherein $R^1$ is selected from the group consisting of: —$(C_1$-$C_{10})$alkyl, —$(C_1$-$C_{10})$halo alkyl, $(C_2$-$C_{10})$alkenyl, $(C_2$-$C_{10})$alkynyl, —O—$(C_1$-$C_{10})$alkyl, —C(O)—O—$(C_1$-$C_{10})$alkyl, aryl, and heteroaryl.

47. The compound of claim 46, wherein $R^1$ is —O—$(C_1$-$C_{10})$alkyl.

48. The compound of claim 47, wherein $R^1$ is $OCH_3$.

49. The compound of claim 43, wherein Ar is an electron rich aryl or heteroaryl ring system.

50. The compound of claim 49, wherein Ar—H is more easily oxidized than benzene.

51. The compound of claim 43, wherein Ar is chosen from a phenylalanine derivative, tyrosine derivative, tryptophan derivative, histidine derivative, and estradiol derivative.

52. The compound of claim 43, wherein the compound of Formula (4) is a compound of Formula (4A):

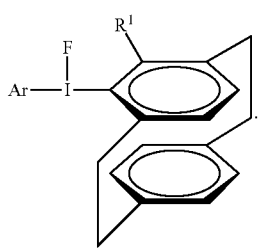

53. The compound of claim 43, wherein the compound of Formula (4) is a compound of Formula (4B):

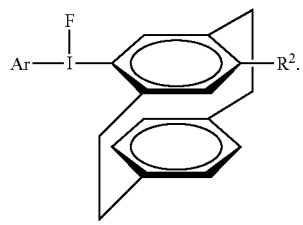

54. The compound of claim 43, wherein Ar is selected from the group consisting of:

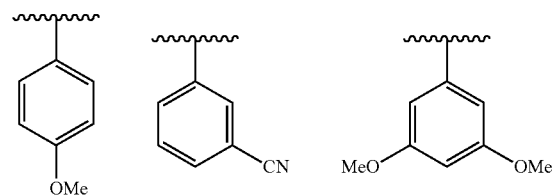

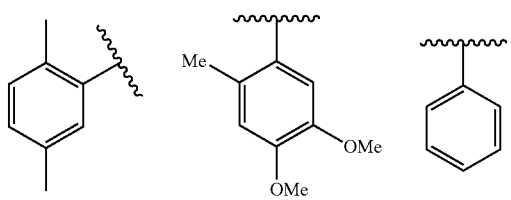

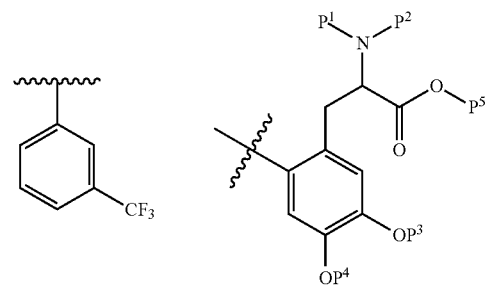

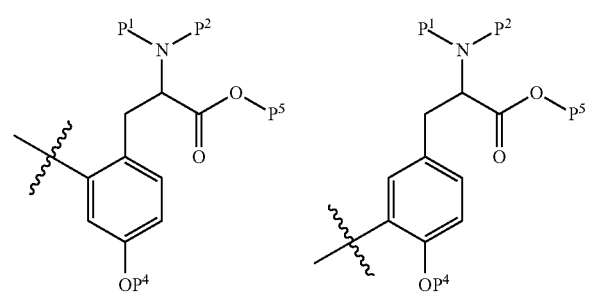

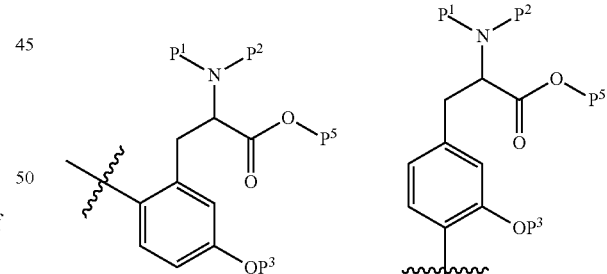

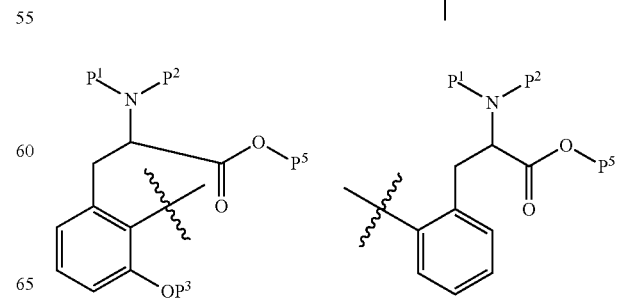

69
-continued
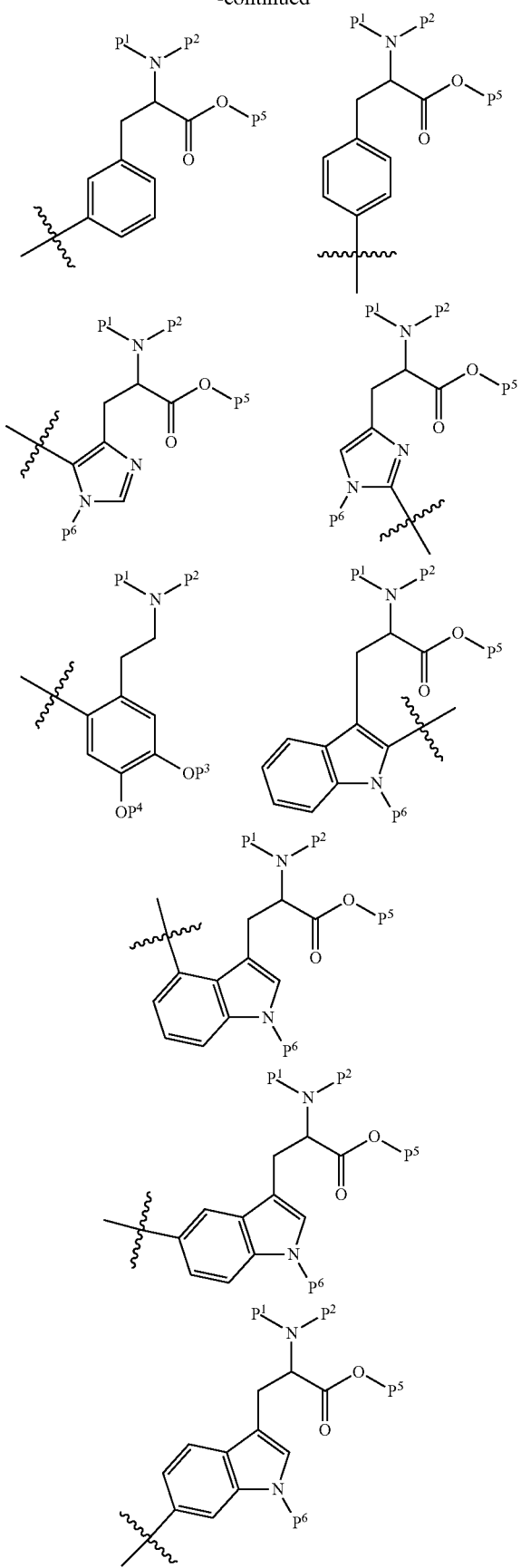
70
-continued
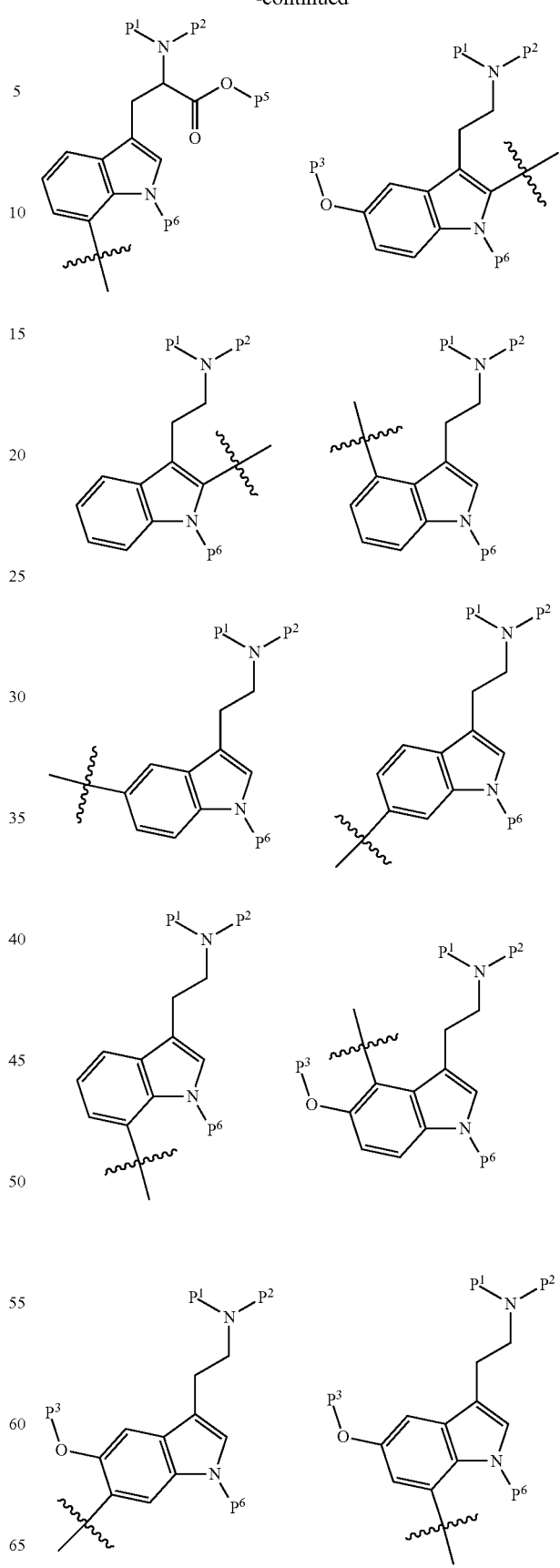

-continued

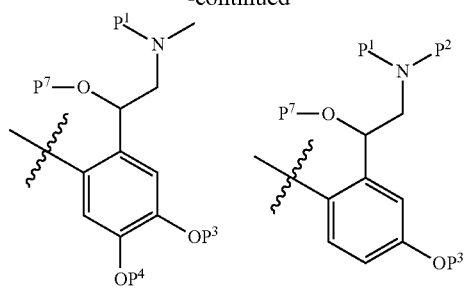

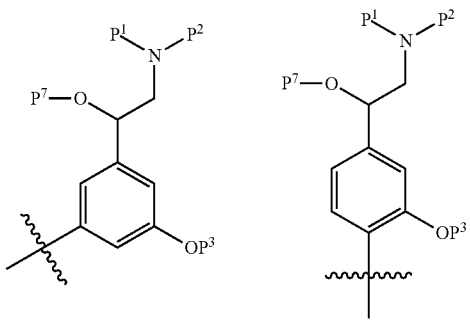

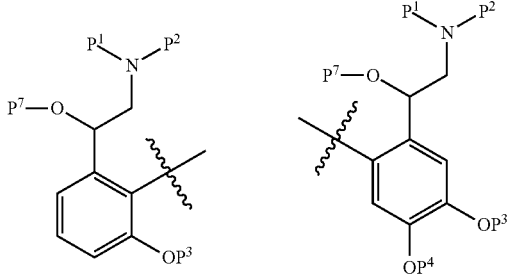

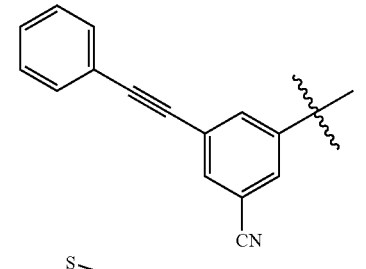

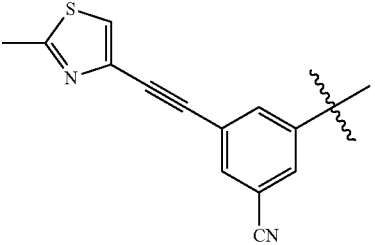

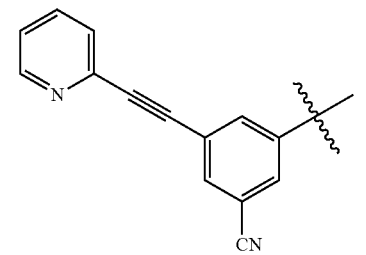

-continued

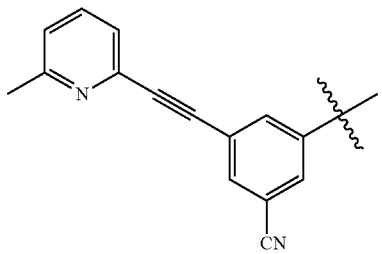

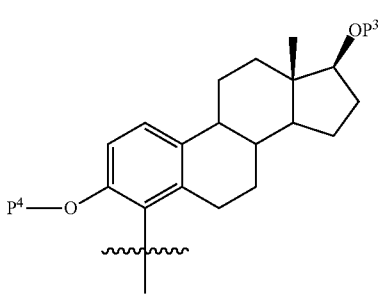

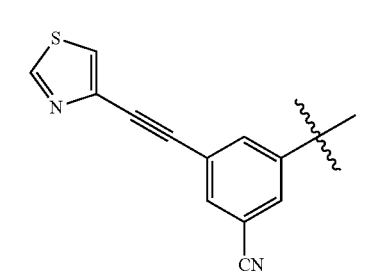

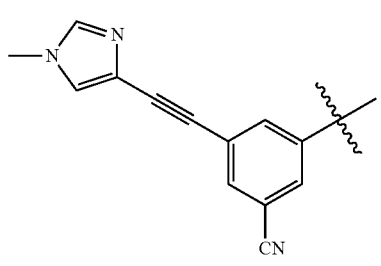

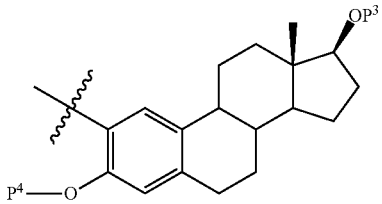

wherein:
  each of $P^1$, $P^2$ and $P^6$ are independently a nitrogen protecting group, or $P^1$ and $P^2$ come together to form a single nitrogen protecting group;
  each of $P^3$, $P^4$, and $P^7$ are independently an alcohol protecting group, or $P^3$ and $P^4$ come together to form a single oxygen protecting group; and
  $P^5$ is a carboxylic acid protecting group.

55. The compound of claim 43, wherein the compound of Formula (4) is selected from the group consisting of:

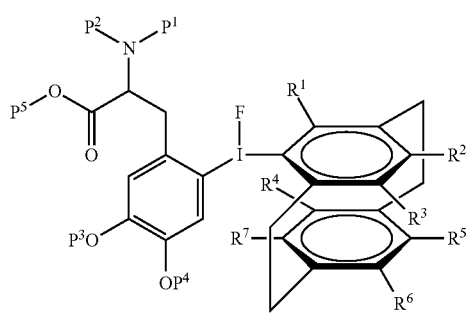

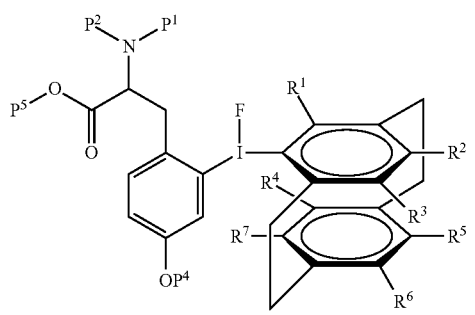

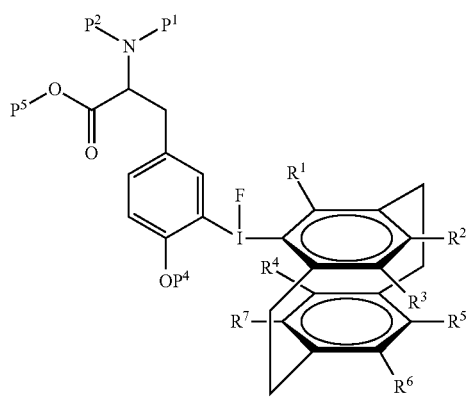

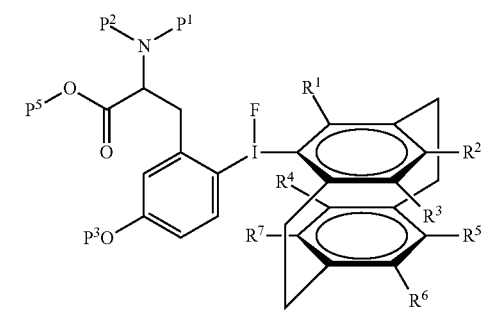

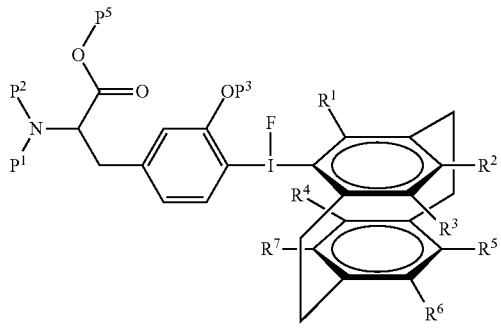

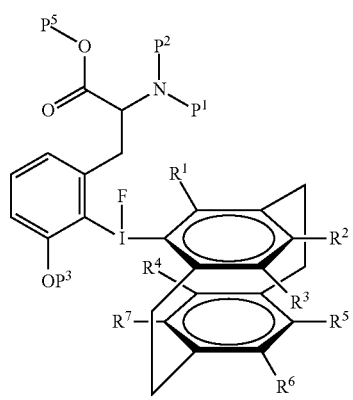

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

56. The compound of claim 43, wherein the compound of Formula (4) is selected from the group consisting of:

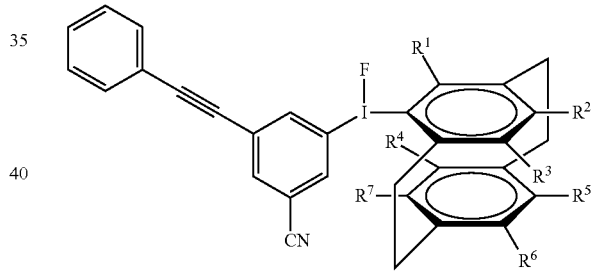

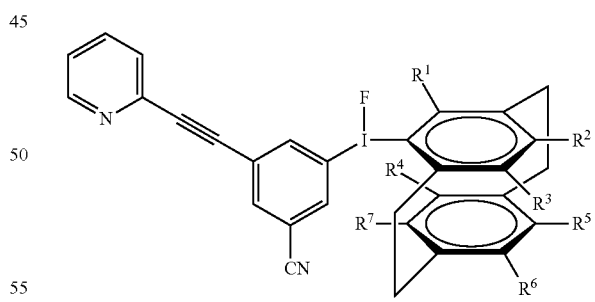

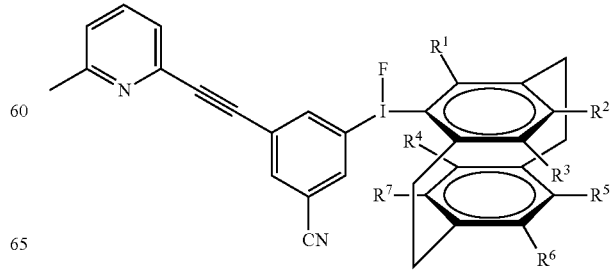

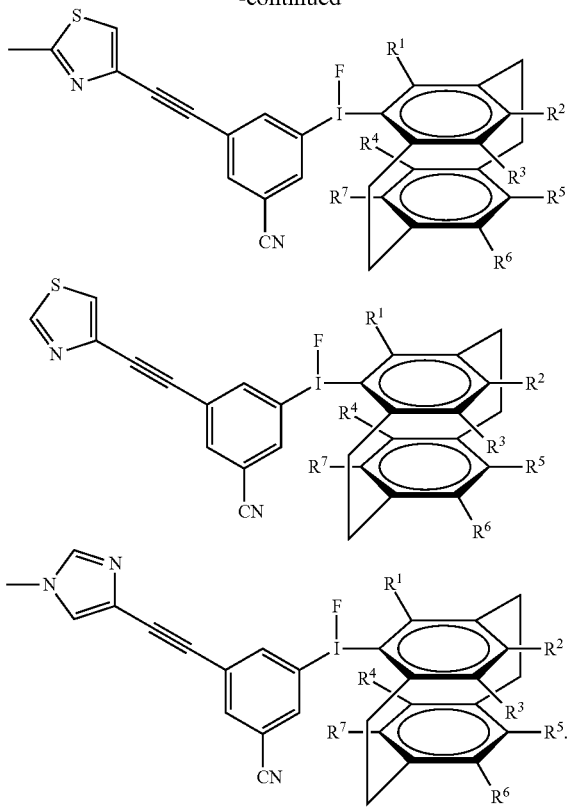

57. The compound of claim 43, wherein the compound of Formula (4) is selected from the group consisting of:

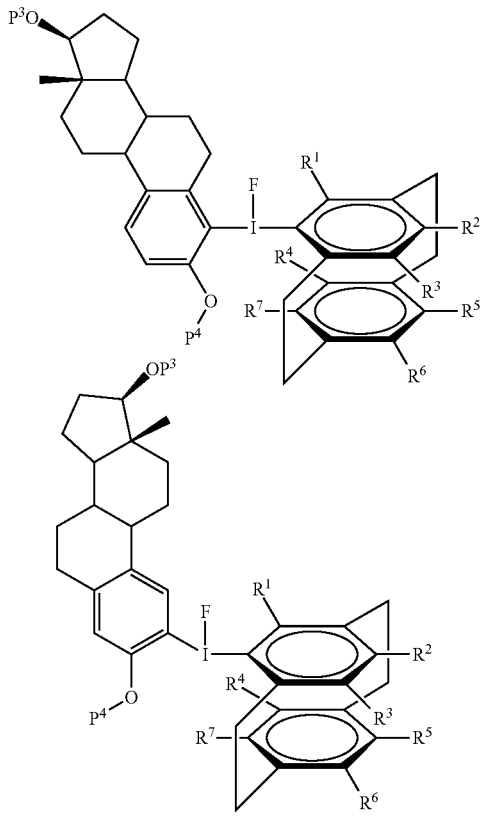

wherein:
each of $P^3$ and $P^4$ are independently an alcohol protecting group.

58. The compound of claim 43, wherein the Ar moiety is enantiomerically enriched.

59. The compound of claim 58, wherein the Ar moiety is present in an enantiomeric excess of at least 75%.

60. The compound of claim 58, wherein the Ar moiety is present in an enantiomeric excess of at least 95%.

61. The compound of claim 58, wherein the Ar moiety is present in an enantiomeric excess of at least 98%.

62. The method of claim 44, wherein M is selected from the group consisting of: potassium; sodium; cesium; complexes of lithium, sodium, potassium, or cesium with cryptands or crown ethers; tetrasubstituted ammonium cations; and phosphonium cations.

63. The method of claim 44, wherein the solution further comprises a non-polar solvent.

64. The method of claim 44, wherein the nonpolar solvent is selected from the group consisting of: benzene, toluene, o-xylene, m-xylene, p-xylene, ethyl benzene, carbon tetrachloride, hexane, cyclohexane, fluorobenzene, chlorobenzene, nitrobenzene, and mixtures thereof.

65. The method of claim 44, wherein the method further comprises filtering the solution to remove insoluble material prior to heating.

66. The method of claim 44, wherein the solvent is removed from the filtrate prior to heating.

67. The method of claim 44, wherein the solution further comprises a polar solvent.

68. The method of claim 67, wherein the polar solvent is chosen from: acetonitrile, acetone, dichloromethane, ethyl acetate, tetrahydrofuran, dimethylformamide, 1,2-difluorobenzene, benzotrifluoride and mixtures thereof.

69. The method of claim 67, wherein the method further comprises filtering the solution to remove insoluble material prior to heating.

70. The method of claim 69, wherein the solvent is removed from the filtrate prior to heating.

71. The method of claim 67, wherein the method further comprises removing salt by chromatography.

72. The method of claim 71, wherein the chromatography is gel permeation chromatography.

73. The method of claim 44, wherein the heating comprises heating at a temperature ranging from about 25° C. to about 250° C.

74. The method of claim 44, wherein the heating occurs for from about 1 second to about 25 minutes.

75. The method of claim 73, wherein the heating is accomplished by a flash pyrolysis method, a conventional heating method, or by a microwave method.

76. The method of claim 44, wherein the compound of Formula (5) is chosen from:

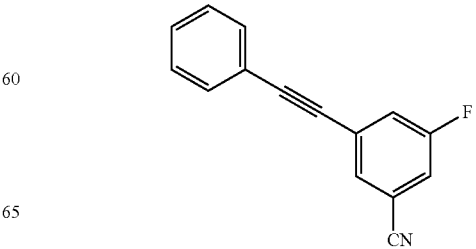

77

-continued

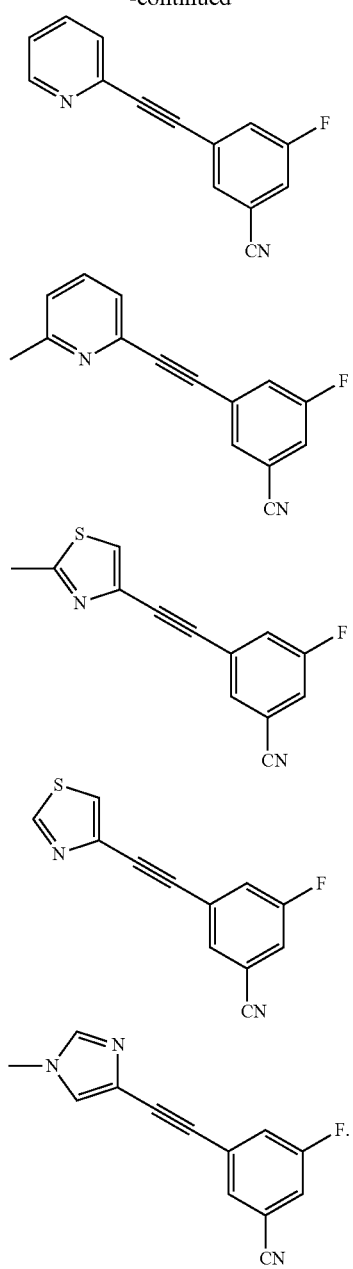

77. The method of claim 44, wherein the compound of Formula (5) is chosen from:

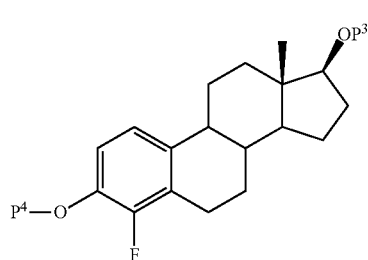

78

-continued

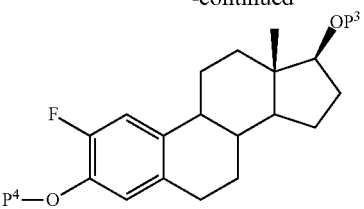

wherein:
each of $P^3$ and $P^4$ are independently an alcohol protecting group.

78. The method of claim 44, wherein the compound of Formula (5) is:

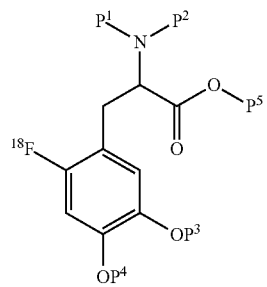

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

79. The method of claim 78, wherein the compound of Formula (5) is:

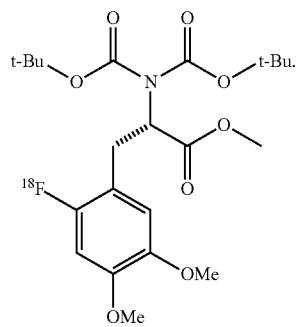

80. The method of claim 44, wherein the compound of Formula (5) is:

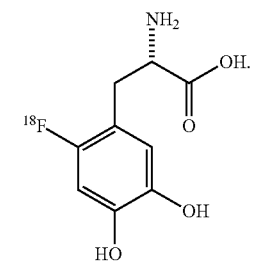 [SMILES: N[C@@H](Cc1cc(O)c(O)cc1[18F])C(=O)O]

81. The method of claim 44, wherein F is $^{18}F$.

82. The method of claim 44, wherein the compound of Formula (3) is a compound of Formula (3A):
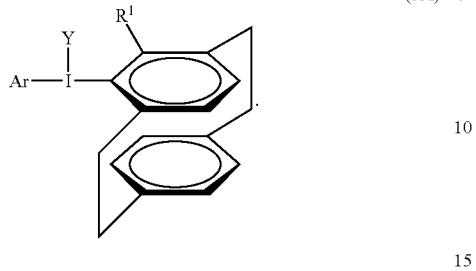
(3A)
83. The method of claim 44, wherein the compound of Formula (3) is a compound of Formula (3B):
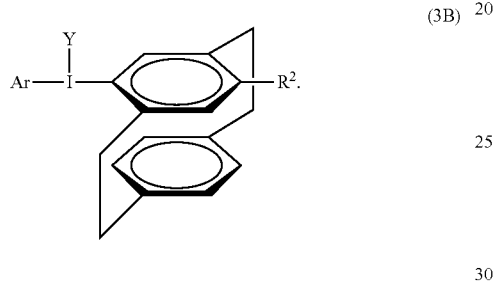
(3B)
* * * * *